United States Patent
Ebright et al.

(10) Patent No.: US 9,060,970 B2
(45) Date of Patent: Jun. 23, 2015

(54) BRIDGE-HELIX CAP: TARGET AND METHOD FOR INHIBITION OF BACTERIAL RNA POLYMERASE

(75) Inventors: Richard H. Ebright, New Brunswick, NJ (US); David Degen, New Brunswick, NJ (US); Katherine Y. Ebright, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/006,035

(22) PCT Filed: Mar. 19, 2012

(86) PCT No.: PCT/US2012/029679
§ 371 (c)(1),
(2), (4) Date: Sep. 18, 2013

(87) PCT Pub. No.: WO2012/129173
PCT Pub. Date: Sep. 27, 2012

(65) Prior Publication Data
US 2014/0018287 A1    Jan. 16, 2014

Related U.S. Application Data

(60) Provisional application No. 61/454,323, filed on Mar. 18, 2011.

(51) Int. Cl.
| | |
|---|---|
| *A61K 45/06* | (2006.01) |
| *C12Q 1/18* | (2006.01) |
| *A61K 38/12* | (2006.01) |
| *C07D 498/08* | (2006.01) |
| *A61K 31/15* | (2006.01) |
| *A61K 31/395* | (2006.01) |
| *A61K 31/155* | (2006.01) |
| *G01N 33/68* | (2006.01) |

(52) U.S. Cl.
CPC .............. *A61K 38/12* (2013.01); *C07D 498/08* (2013.01); *G01N 2333/91275* (2013.01); *C12Q 1/18* (2013.01); *A61K 31/15* (2013.01); *A61K 31/395* (2013.01); *A61K 31/155* (2013.01); *A61K 45/06* (2013.01); *G01N 33/68* (2013.01)

(58) Field of Classification Search
CPC .................. C07D 498/08; G01N 2333/91275; G01N 33/68; C12Q 1/18; A61K 31/15; A61K 31/395; A61K 2300/00; A61K 31/155; A61K 38/12; A61K 45/06
See application file for complete search history.

(56) References Cited

U.S. PATENT DOCUMENTS

2010/0047780 A1 * 2/2010 Ebright ................... 435/6
2010/0120896 A1   5/2010 Sander et al.

FOREIGN PATENT DOCUMENTS

| WO | WO 2004/023093 A2 | 3/2004 |
|---|---|---|
| WO | WO 2005/001034 A2 | 1/2005 |
| WO | WO 2007/089310 A1 | 8/2007 |
| WO | WO 2007/094799 A1 | 8/2007 |

OTHER PUBLICATIONS

Definition of derivative, from http://cancerweb.ncl.ac.uk/omd/about.html, pp. 1-5, accessed Jul. 7, 2005.*
Weinzierl, The nucleotide addition cycle of RNA polymerase is controlled by two molecular hinges in the Bridge Helix domain, BMC Biology, 2010, 8, pp. 1-15, published on Oct. 29, 2010.*
Degen et al, Transcription inhibition by the depsipeptide antibiotic salinamide A, eLife, 2014, 3, pp. 1-29.*
Artsimovitch et al., "A new class of bacterial RNA polymerase inhibitor affects nucleotide addition", *Science* 302, 650-654 (2003).
Austin et al., "Genetic Analysis of Lipopolysaccharide Core Biosynthesis by *Escherichia coli* K-12: Insertion Mutagenesis of the rfa Locus", *Journal of Bacteriology* vol. 172 (9), 5312-5325, (1990).
Baquero et al., "Polymorphic mutation frequencies in *Escherichia coli*", *J. Bacteriol.*, 186, 5538-5542 (2004).
Campbell et al., "Structural mechanism for rifampicin inhibition of bacterial RNA polymerase", *Cell* 104, 901-912 (2001).
Chopra, I. "Bacterial RNA polymerase: a promising target for the discovery of new antimicrobial agents", *Curr. Opin. Investig. Drugs* 8, 600-607 (2007).
Fralick et al., "Additive effect of tolC and rfa mutations on the hydrophobic barrier of the outer membrane of *E. coli* K-12", *J. Bacteriol.* 176, 6404-6406 (1994).
Hein et al., "The bridge helix coordinates movements of modules in RNA polymerase", *BMC Biol.* 8, 141, 5 pages (2010).
Ho et al., "Structures of RNA polymerase-antibiotic complexes", *Curr. Opin. Structl. Biol. 19*, 715-723 (2009).
Jin et al., "Mapping and sequencing of mutations in the *Escherichia coli* rpoB gene that lead to rifampicin resistance", *J. Mol. Biol.* 202, 45-58 (1988).
King et al., "Macromolecular synthesis and membrane perturbation assays for mechanisms of action studies of antimicrobial agents", *Curr. Protoc. Pharmacol.* 47, 13A.7.1-13A.7.23 (2009).

(Continued)

*Primary Examiner* — Julie Ha
*Assistant Examiner* — Li Ni Komatsu
(74) *Attorney, Agent, or Firm* — Viksnins Harris & Padys PLLP

(57) ABSTRACT

It has been discovered that the Sal target represents a new and promising target for antibacterial drug discovery. The Sal target is distinct from the rifamycin target and from the CBR703 target. This indicates that antibacterial compounds that function through the Sal target should exhibit no, or minimal, cross-resistance with rifamycins and CBR703. This further implies that it should be possible to co-administer antibacterial compounds that function through the Sal target together with a rifamycin, together with CBR703, or together with both a rifamycin and CBR703, in order to achieve additive or synergistic antibacterial effects and in order to suppress or eliminate the emergence of resistance.

19 Claims, 9 Drawing Sheets

(56) References Cited

OTHER PUBLICATIONS

Lane et al., "Molecular evolution of multisubunit RNA polymerases: sequence analysis", *J. Mol. Biol. 395*, 671-85 (2010).

Miao et al., "Inhibition of bacterial RNA polymerases: peptide metabolites from the cultures of *Streptomyces* sp.", *J. Nat. Prod. 60*, 858-861 (1997).

Moore et al., "Biosynthesis of the bicyclic depsipeptide salinamide A in *Streptomyces* sp. CNB-091: origin of the carbons", *Tetrahedron Lett. 39*, 3915-3918 (1998).

Moore et al., "Salinamides: antiinflammatory depsipeptides from a marine streptomycete", *J. Org. Chem.*, 64, 1145-1150 (1999).

Mukhopadhyay et al., "The RNA polymerase "switch region" is a target for inhibitors", *Cell 135*, 295-307 (2008).

Ovchinnikov et al., "Primary structure of *Escherichia coli* RNA polymerase nucleotide substitution in the β subunit gene of the rifampicin resistant rpoB255 mutant", *Mol. Gen. Genet. 184*, 536-538 (1981).

Ovchinnikov et al., "RNA polymerase rifampicin resistance mutations in *Escherichia coli*: sequence changes and dominance", *Mol. Gen. Genet. 190*, 344-348 (1983).

Patent Cooperation Treaty, International Searching Authority, Search Report and Written Opinion for PCT/US2012/29679, 15 pages, Jun. 14, 2012.

Severinov et al., "Rifampicin region revisited: new rifampicin-resistant and streptolydigin-resistant mutants of the β subunit of *Escherichia coli* RNA polymerase", *J. Biol. Chem. 268*, 14820-14825 (1993).

Tan et al., "Total synthesis of salinamide A: a potent anti-inflammatory bicyclic depsipeptide", *Angew. Chem. Int. Ed. 47*, 3614-3617 (2008).

Trischman et al. "Salinamides A and B: anti-inflammatory depsipeptides from a marine streptomycete", *J. Am. Chem. Soc.*, 116, 757-758 (1994).

Tuske et al., "Inhibition of Bacterial Rna Polymerase by Streptolydigin: Stabilizaiton of a Straight-Bridge-Helix Active-Center Conformation" *Cell*, vol. 122 (4), 541-552 (2005).

Vassylyev et al., "Crystal structure of a bacterial RNA polymerase holoenzyme at 2.6 Å resolution", *Nature 417*, 712-719 (2003).

Vassylyev et al., "Structural basis for substrate loading in bacterial RNA polymerase", *Nature 448*, 163-168 (2007).

Villain-Guillot et al., "Progress in targeting bacterial transcription", *Drug Discov. Today 12*, 200-208.23 (2007).

Weinzierl "The nucleotide addition cycle of RNA polymerase is controlled by two molecular hinges in the Bridge Helix domain", *BMC Biol. 8*, 134, 16 pages (2010).

\* cited by examiner

| | | | | |
|---|---|---|---|---|
| RPOC_ECOLI | (687) | AAANDRVSKAMMDN | (735) | AQIRQLA |
| RPOC_HAEIN | (688) | AAANERVAKAMMEN | (736) | AQIRQLA |
| RPOC_VIBCH | (687) | ASTNDRVAKAMWEN | (735) | AQIRQLA |
| RPOC_PSEAE | (687) | SKANDEVSKAMMAN | (735) | AQIRQLA |
| RPOC_TREPA | (665) | SKTSEELTSIMMET | (702) | NQIRQLA |
| RPOC_BORBU | (661) | LKTNEELTNKWWEI | (698) | NQIRQLA |
| RPOC_XYLFA | (710) | SRTNERIAKAMMDT | (758) | AQIRQLA |
| RPOC_CAMJE | (696) | KSTNNVLSKEMMKL | (733) | AQIRQLA |
| RPOC_NEIMA | (689) | GRAGDKIAKAMMDN | (737) | AQEKQLS |
| RPOC_RICPR | (685) | SRCTDRVANDMMKE | (729) | QQIKQLG |
| RPOC_CHLTR | (697) | TEVSDILLSNALYSE | (735) | SQLKQLG |
| RPOC_MYCPN | (782) | NGVKEKVSSEIQDL | (819) | SNFTQLF |
| RPOC_BACSU | (706) | SAAKDVIQGKLMKS | (739) | SNFIQLA |
| RPOC_STAAU | (710) | TDAKDQIQGELMQS | (743) | SNFIQLA |
| RPOC_MYCTU | (779) | KEATDEVGQALREH | (812) | TQTRTLA |
| RPOC_SYNY3 | (726) | NGTSEELKDQVVVN | (762) | SQVRQLV |
| RPOC_AQUAE | (803) | SEATNLVSKAMFEE | (849) | DQIRQLA |
| RPOC_DEIRA | (1015) | NNTTDAVKDAVFEN | (1051) | QQIRQLA |
| RPOC_THEAQ | (997) | TETTEKYTQAVFKN | (1033) | QQIRQLC |
| RPOC_TTHER | (997) | TETTEKYTQAVFKN | (1033) | QQIRQLC |
| RPA1_HUMAN | (859) | NMIDLKFKEEWNHY | (907) | VNTMQIS |
| RPB1_HUMAN | (738) | ENQMNRILNDARDK | (779) | INHSQVI |
| RPC1_HUMAN | (749) | EALITKELSVIRDH | (790) | INHSQMI |

| | | D2 LOOP | | LINK REGION | |
|---|---|---|---|---|---|
| RPOB_ECOLI | (566) | GPNIGLI (569) | (672) | EHDDANRAL (675) | Bacterial RNAP |
| RPOB_HAEIN | (566) | GPNIGLI | (673) | EHDDANRAL | |
| RPOB_VIBCH | (600) | GPNIGLI | (706) | EHDDANRAL | |
| RPOB_PSEAE | (571) | GPNIGLI | (677) | EHDDANRAL | |
| RPOB_TREPA | (537) | GPNIGLI | (643) | EHDDANRAL | |
| RPOB_BORBU | (518) | GPNIGLI | (624) | EHDDANRAL | |
| RPOB_XYLFA | (598) | GPNIGLI | (704) | EHDDANRAL | |
| RPOB_CAMJE | (581) | GQNIGLI | (687) | EHDNDANRAL | |
| RPOB_NEIMA | (593) | GQNIGLI | (699) | EHDDANRAL | |
| RPOB_RICPR | (583) | GQNIGLI | (690) | EHDDSARAL | |
| RPOB_CHLTR | (511) | GPNIGLI | (617) | ENDDSNRAL | |
| RPOB_MYCPN | (664) | GMNIGLI | (772) | ENDDSNRAL | |
| RPOB_BACSU | (522) | GPNIGLI | (630) | EHDDANRAL | |
| RPOB_STAAU | (521) | GPNIGLI | (629) | EHDDANRAL | |
| RPOB_MYCTU | (491) | GPNIGLI | (598) | EHDDANRAL | |
| RPOB_SYNY3 | (420) | GPNAGLI | (528) | EHDDANRAL | |
| RPOB_AQUAE | (648) | GQNIGLV | (753) | EHDDANRAL | |
| RPOB_DEIRA | (495) | GANIGLI | (601) | EHDDANRAL | |
| RPOB_TTHER | (446) | GANIGLI | (551) | EHDDANRAL | |
| RPOB_THEAQ | (446) | GANIGLI | (551) | EHDDANRAL | |
| RPA2_HUMAN | (449) | GEPCGLM | (622) | DHNQSPRNM (677) | Human RNAP I, II, III |
| RPB2_HUMAN | (517) | GHAWGLV | (715) | DHNQSPRNT | |
| RPC2_HUMAN | (487) | GEAQGLV | (676) | HHNQSPRNT (680) | |

FIG. 4C

BRIDGE-HELIX CAP: TARGET AND METHOD FOR INHIBITION OF BACTERIAL RNA POLYMERASE

CROSS-REFERENCE TO RELATED APPLICATION(S)

This patent application claims the benefit of priority of U.S. application Ser. No. 61/454,323, filed Mar. 18, 2011, which application is herein incorporated by reference.

Sequence Listing

The instant application contains a Sequence Listing which has been submitted in ASCII format via EFS-Web and is hereby incorporated by reference in its entirety. Said ASCII copy, is named 83503WO1.txt and is 29,392 bytes in size.

STATEMENT OF GOVERNMENT SUPPORT

This invention was made with government support under Grant #R01-GM41376 and Grant #R01-AI72766 awarded by the National Institutes of Health. The government has certain rights in the invention.

BACKGROUND

Bacterial infections remain among the most common and deadly causes of human disease. Multi-drug-resistant bacteria now cause infections that pose a grave and growing threat to public health. It has been shown that bacterial pathogens can acquire resistance to first-line and even second-line antibiotics. New approaches to drug development for treating bacterial infections are necessary, e.g., to combat the ever-increasing number of antibiotic-resistant pathogens.

SUMMARY OF CERTAIN EMBODIMENTS OF THE INVENTION

We disclose here that the antibiotic salinamide A (Sal) inhibits bacterial RNA polymerase (RNAP) in vivo, that Sal kills bacteria by inhibiting RNAP, and how Sal inhibits RNAP. To determine whether Sal inhibits RNAP in vivo, effects of Sal on RNAP activity in vivo were assayed. Upon addition of Sal to bacteria, RNAP-dependent RNA synthesis decreased immediately, indicating that Sal inhibits RNAP in vivo. To determine whether Sal kills bacteria by inhibiting RNAP, spontaneous Sal-resistant mutants of were isolated, and genes for RNAP subunits in Sal-resistant mutants were amplified and sequenced. One hundred percent (39 of 39) of analyzed Sal-resistant mutants contained mutations in genes encoding RNAP subunits, indicating that Sal kills bacteria by inhibiting RNAP. Substitutions conferring Sal-resistance were obtained at positions 690, 697, 738, 748, 758, 763, 779, 780, 782, and 783 of *Escherichia coli* RNAP β'-subunit and positions 569, 675, and 677 of *Escherichia coli* RNAP β-subunit. Additional Sal-resistant mutants were isolated following mutagenesis of genes encoding RNAP subunits. In these additional Sal-resistant mutants, substitutions conferring Sal-resistance were identified at positions 758, 780, and 782 of *Escherichia coli* RNAP β' subunit and positions 561, 665, and 680 of *Escherichia coli* RNAP β subunit.

When mapped onto the structure of RNAP, the sites of substitutions conferring Sal-resistance formed a compact cluster. We designate the sites of substitutions conferring Sal-resistance as the "Sal target."

Determination of a crystal structure of *Escherichia coli* RNAP in complex with Sal showed that the Sal target is the binding site on RNAP for Sal, and that sites of substitutions conferring Sal-resistance correspond to RNAP residues of RNAP that contact, or are close to, Sal.

The Sal target does not overlap the targets of currently used antibiotics. Accordingly, Sal does not exhibit cross-resistance with currently used antibiotics, and coadministration of Sal with a currently used antibiotic results in an extremely low spontaneous resistance frequency. The Sal target represents an attractive new target for antibacterial drug discovery.

A subset of residues of the Sal target have no overlap with any previously described target of any previously described RNAP inhibitor: i.e., residues 690, 697, 758, and 763 of *Escherichia coli* RNAP β' subunit and residues 561, 569, 665, 675, 677, and 680 of *Escherichia coli* RNAP β subunit. In the structure of RNAP, these residues are located in proximity to the N-terminus of the RNAP-active-center bridge helix, in and near RNAP-active-center sub-regions termed the "β' F loop," the "β D2 loop," and the "β link region" (FIG. 4). We designate these residues as the "bridge-helix cap target."

In RNAP from *Escherichia coli*, the bridge-helix cap target comprises residues 690, 697, 758, and 763 of *Escherichia coli* RNAP β' subunit and residues 561, 569, 665, 675, 677, and 680 of *Escherichia coli* RNAP β subunit. In RNAP from other bacterial species, the bridge-helix cap target comprises the residues corresponding to, and alignable with, residues 690, 697, 758, and 763 of *Escherichia coli* RNAP β' subunit and residues 561, 569, 665, 675, 677, and 680 of *Escherichia coli* RNAP β subunit (FIG. 4). For example, in RNAP from *Bacillus subtilis*, the bridge-helix cap target comprises the residues corresponding to, and alignable with, residues 709, 716, 762, and 767 of *Bacillus subtilis* RNAP β' subunit and residues 517, 525, 623, 633, 635, and 638 of *Bacillus subtilis* RNAP β subunit (FIG. 4).

Accordingly, certain embodiments of the present invention provide (i) a target for binding of a molecule to an RNA polymerase from a bacterial species, comprising at least one residue corresponding to, and alignable with, residues 561, 569, 665, 675, 677, and 680 of the β subunit and residues 690, 697, 758, and 763 of the β' subunit of RNA polymerase from *Escherichia coli* ("bridge-helix cap target");

(ii) a target for inhibition by a molecule of an RNA polymerase from a bacterial species, comprising at least one residue corresponding to, and alignable with, residues 561, 569, 665, 675, 677, and 680 of the β subunit and residues 690, 697, 758, and 763 of the β' subunit of RNA polymerase from *Escherichia coli* ("bridge-helix cap target");

(iii) a method to identify a molecule that binds to the target of i and ii comprising identification of a molecule that (a) binds to an RNA polymerase from a bacterial species, but (b) does not bind, or binds less well, to a derivative of an RNA polymerase from a bacterial species that has at least one amino acid substitution, deletion, or insertion, in the set of residues taught in i and ii;

(iv) a method to identify a molecule that inhibits an RNA polymerase from a bacterial species through the target of i and ii, comprising identification of a molecule that (a) inhibits an RNA polymerase from a bacterial species, but (b) does not inhibit, or inhibits less well, a derivative of an RNA polymerase from a bacterial species that has at least one amino acid substitution, deletion, or insertion, in the set of residues taught in i and ii;

(v) a method to identify a molecule that inhibits growth of a bacterium through the target of i and ii, comprising identification of a molecule that (a) inhibits growth of a bacterium, but (b) does not inhibit, or inhibits less well, a derivative of said bacterium that contains a derivative of an RNA polymerase that has at least one amino acid substitution, deletion, or insertion, in the set of residues taught in i and ii; and (vi) a method to identify a molecule that binds to an RNA polymerase from a bacterial species through the target of i and ii, comprising (a) preparation of a first molecule that binds to the target of i and ii and that contains a detectable group, and (b) identification of a second molecule that competes with said first molecule for binding to an RNA polymerase from a bacterial species.

(vii) a method to treat a bacterial infection in a subject in need thereof, comprising administering to the subject a first compound selected as being an inhibitor of growth of a bacterium by binding to the target of i and ii, and a second compound that inhibits growth of a bacterium by binding to a site other than the target of i and ii.

BRIEF DESCRIPTION OF THE FIGURES

FIG. 4. Sal target: location in the amino acid sequence of RNAP β' and β subunits. Amino acid sequence alignments for regions of *E. coli* RNAP β' subunit (top panel) and β subunit (bottom panel) containing single-residue substitutions that confer Sal-resistance (see Tables 2-3). Sequences for bacterial RNAP are in the top twenty rows of each panel (Top panel sequences for bacterial RNAP are disclosed as SEQ ID NOS 5-64, respectively, in order of appearance. Bottom panel sequences for bacterial RNAP are disclosed as SEQ ID NOS 74-113, respectively, in order of appearance.); sequences for human RNAP I, RNAP II, and RNAP III are in the bottom three rows (Top panel sequences for human RNAP I, RNAP II, and RNAP III are disclosed as SEQ ID NOS 65-73, respectively, in order of appearance. Bottom panel sequences for human RNAP I, RNAP II, and RNAP III are disclosed as SEQ ID NOS 114-119, respectively, in order of appearance.); sites of single-residue substitutions that confer Sal-resistance are boxed (with *E. coli* residue numbers); RNAP active-center sub-regions are indicated with black bars above the sequences. Species are as follows: *E. coli* (ECOLI), *Haemophilus influenzae* (HAEIN), *Vibrio cholerae* (VIBCH), *Pseudomonas aeruginosa* (PSEAE), *Treponema pallidum* (TREPA), *Bordetella pertussis* (BORPE), *Xylella fastidiosa* (XYLFA), *Campylobacter jejuni* (CAMJE), *Neisseria meningitidis* (NEIME), *Rickettsia prowazekii* (RICPR), *Chlamydia trachomatis* (CHLTR), *Mycoplasma pneumoniae* (MYCPN), *Bacillus subtilis* (BACSU), *Staphylococcus aureus* (STAAU), *Mycobacterium tuberculosis* (MYCTU), *Synechocystis* sp. PCC 6803 (SYNY3), *Aquifex aeolicus* (AQUAE), *Deinococcus radiodurans* (DEIRA), *Thermus aquaticus* (THEAQ), *Thermus thermophilus* (THETH), and *Homo sapiens* (HUMAN).

DETAILED DESCRIPTION

Figure 1:
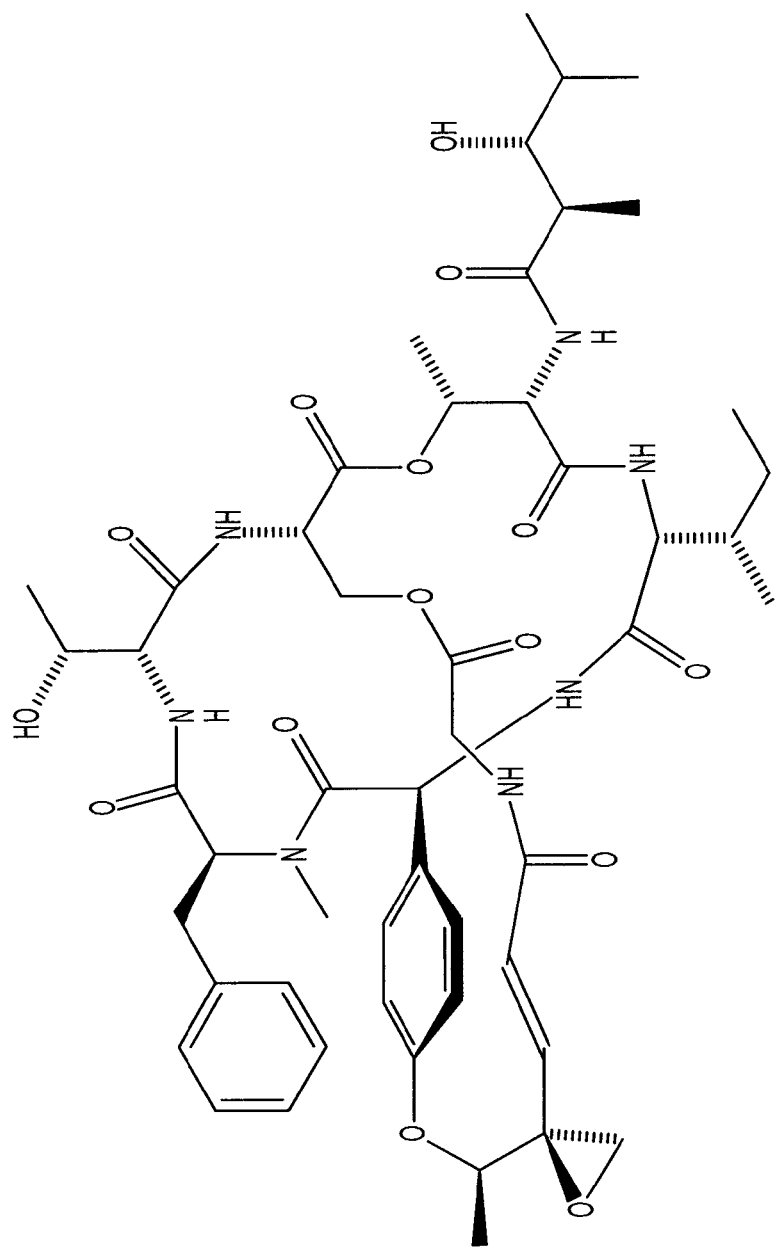
FIG. 1. Structure of Sal.

It has been discovered that the bridge-helix cap target represents a new and promising target for antibacterial drug discovery. The bridge-helix cap target is distinct from the rifamycin target and from the CBR703 target. This implies that antibacterial compounds that function through the bridge-helix cap target should exhibit no, or minimal, cross-resistance with rifamycins and CBR703. This further implies that it should be possible to co-administer antibacterial compounds that function through the bridge-helix cap target together with a rifamycin, together with CBR703, or together with both a rifamycin and CBR703, in order to achieve additive or super-additive/synergistic antibacterial effects and in order to suppress or eliminate the emergence of resistance.

Accordingly, certain embodiments of the present invention provide a method to identify a molecule that binds to the bridge-helix cap target of an RNA polymerase from a bacterial species, comprising identifying a molecule that binds to an RNA polymerase from a bacterial species but binds substantially less to a derivative of an RNA polymerase from a bacterial species that has at least one amino acid substitution, deletion, or insertion of at least one residue corresponding to, or alignable with, residues 561, 569, 665, 675, 677, or 680 of the β subunit or residues 690, 697, 758, or 763 of the β' subunit of RNA polymerase from *Escherichia coli*.

Certain embodiments of the present invention provide a method to identify a molecule that inhibits an RNA polymerase from a bacterial species by binding to the bridge-helix cap target of the RNA polymerase, comprising identifying a molecule that inhibits an RNA polymerase from a bacterial species but inhibits substantially less a derivative of an RNA polymerase from a bacterial species that has at least one amino acid substitution, deletion, or insertion of at least one residue corresponding to, or alignable with, residues 561, 569, 665, 675, 677, or 680 of the β subunit or residues 690, 697, 758, or 763 of the β' subunit of RNA polymerase from *Escherichia coli*.

Certain embodiments of the present invention provide a method to identify a molecule that inhibits growth of a bacterium, comprising identifying a molecule that inhibits growth of a bacterium but inhibits growth substantially less of a derivative of said bacterium that has at least one amino acid substitution, deletion, or insertion of at least one residue corresponding to, or alignable with, residues 561, 569, 665, 675, 677, or 680 of the β subunit or residues 690, 697, 758, or 763 of the β' subunit of RNA polymerase from *Escherichia coli*.

Certain embodiments of the present invention provide a method to identify a molecule that binds to an RNA polymerase from a bacterial species through the bridge-helix cap target of the RNA polymerase, comprising identifying a target molecule that competes with a first molecule for binding to an RNA polymerase from a bacterial species, wherein the first molecule preferentially binds to the bridge-helix cap target of the RNA polymerase.

In certain embodiments, the first molecule comprises a detectable group.

Certain embodiments of the present invention provide a method to treat a bacterial infection in a subject in need thereof, comprising administering to the subject a first compound selected as being an inhibitor of growth of a bacterium by binding to the bridge-helix cap target of an RNA polymerase, and a second compound that inhibits growth of a bacterium by binding to a site other than the bridge-helix cap target of an RNA polymerase.

In certain embodiments, the first compound is salinamide A.

In certain embodiments, the second compound is a rifamycin or CBR703.

In certain embodiments, the method further comprises administering a third compound that inhibits growth of a bacterium by binding to a site other than the bridge-helix cap target of an RNA polymerase.

In certain embodiments, the first and second compounds are administered concurrently.

In certain embodiments, the first and second compounds are administered sequentially.

In certain embodiments, the third compound is administered concurrently.

In certain embodiments, the third compound is administered sequentially.

Certain embodiments of the present invention provide a composition (e.g., a pharmaceutical composition), or a kit, that comprises salinamide A and a rifamycin and/or CBR703.

In certain embodiments, the composition or kit comprises salinamide A and a rifamycin.

In certain embodiments, the composition or kit comprises salinamide A and CBR703.

In certain embodiments, the composition or kit comprises salinamide A, a rifamycin and CBR703.

Certain embodiments of the present invention provide a method to treat a bacterial infection in a subject in need thereof, comprising administering to the subject a composition described herein.

Certain embodiments of the present invention provide the use of a composition described herein to treat a bacterial infection.

Certain embodiments of the present invention provide an RNA polymerase, e.g., an isolated RNA polymerase, that has at least one amino acid substitution, deletion, or insertion of at least one residue corresponding to, or alignable with, residues 561, 569, 665, 675, 677, or 680 of the β subunit or residues 690, 697, 758, or 763 of the β' subunit of RNA polymerase from *Escherichia coli*.

Certain embodiments of the present invention provide a bacterium, e.g., an isolated bacterium, that comprises an RNA polymerase that has at least one amino acid substitution, deletion, or insertion of at least one residue corresponding to, or alignable with, residues 561, 569, 665, 675, 677, or 680 of the β subunit or residues 690, 697, 758, or 763 of the β' subunit of RNA polymerase from *Escherichia coli*.

Provided herein are targets and methods for specific binding and inhibition of RNA polymerase from bacterial species. Embodiments of the invention have applications in control of bacterial gene expression, control of bacterial growth, antibacterial chemistry, and antibacterial therapy.

Certain embodiments of the invention include: a new target (the bridge-helix cap target) and associated assay methods for inhibition of bacterial RNA polymerase, inhibition of bacterial RNA synthesis and inhibition of bacterial growth. Antibacterial compounds that function through the new target should exhibit minimal or no cross-resistance with antibacterial compounds that function through previously disclosed targets. It should be possible to co-administer antibacterial compounds that function through the new target together with antibacterial compounds that function through previously disclosed targets, to achieve additive antibacterial effects and to suppress the emergence of resistance.

Certain embodiments of the invention will now be illustrated by the following non-limiting Example.

Example 1

Identification of the Target of the Antibiotic Salinamide A

Salinamide A (Sal) is a bicyclic depsipeptide antibiotic, comprising seven amino acids and two non-amino-acid residues (1, 2; FIG. 1). Sal is produced by *Streptomyces* sp. CNB-091, a marine bacterium isolated from the surface of the jellyfish *Cassiopeia xamachana* (1-3), and also by *Streptomyces* sp. NRRL 21611, a soil bacterium (4). Sal exhibits antibacterial activity against bacterial pathogens including *Streptococcus pneumoniae* and *S. pyogenes* (1, 2).

Sal has been reported to inhibit bacterial RNA polymerase (RNAP), the enzyme responsible for bacterial RNA synthesis, in vitro ($IC_{50}$=0.5 µM; 4). However, it has not previously been determined whether RNAP is the functional cellular target of Sal.

The hypothesis of this research was that RNAP is the functional cellular target of Sal. Corollaries to this hypothesis were that Sal should inhibit RNAP in vivo, that mutations conferring resistance to Sal should occur in RNAP-subunit genes, and that mapping of sites of substitutions conferring resistance to Sal onto the three-dimensional structure of RNAP should define residues of RNAP important for function of Sal. The objectives of this research were to determine whether Sal inhibits RNAP in vivo, to determine whether Sal kills bacteria by inhibiting RNAP, and to determine how Sal inhibits RNAP.

Figure 2:
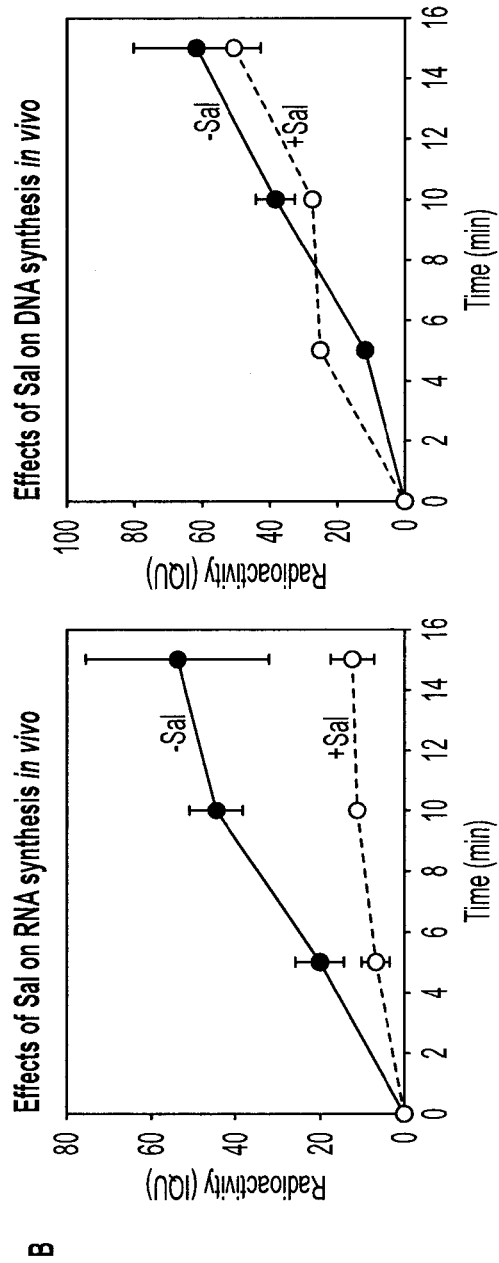
FIG. 2. Measurement of effects of Sal on nucleic acid synthesis in vivo. (A) Experimental approach. (B) Effects of Sal on RNA (left) and DNA (right) synthesis in vivo.
Figure 3:
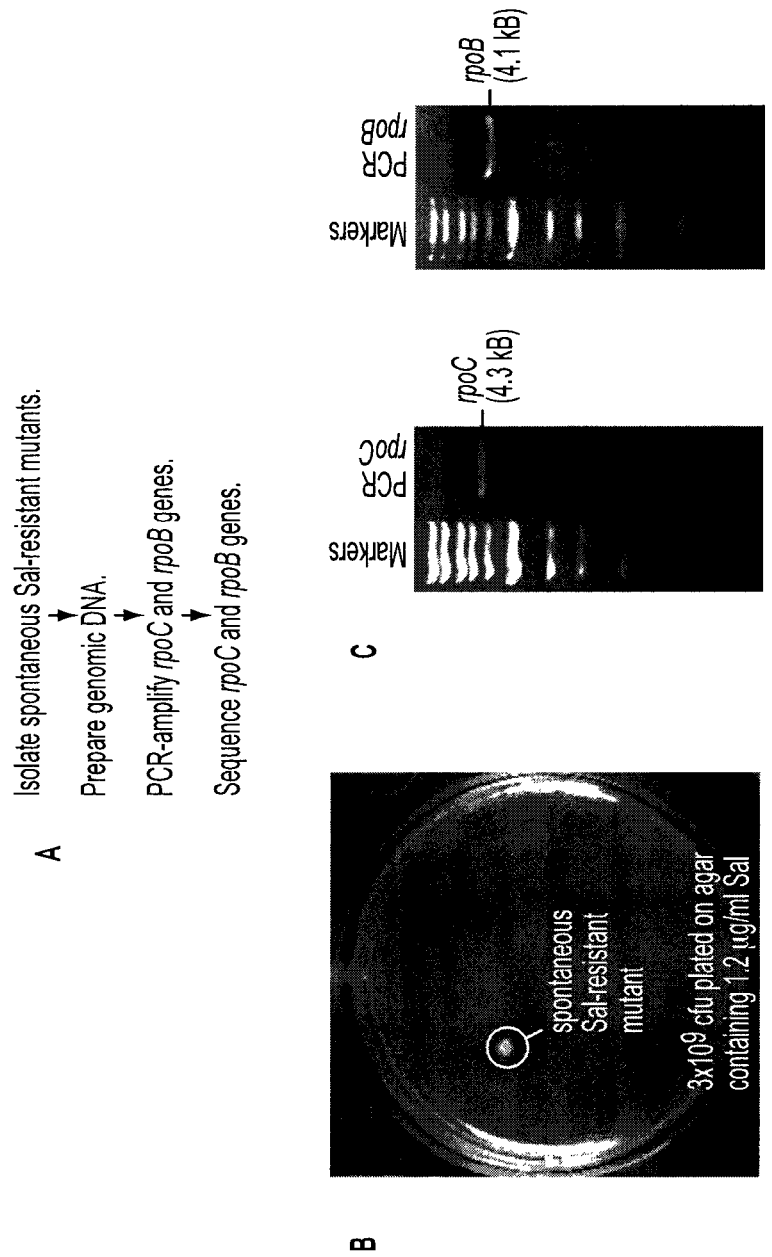
FIG. 3. Isolation of spontaneous Sal-resistant mutants, followed by PCR-amplification and sequencing of RNAP-subunit genes. (A) Experimental approach. (B) Representative data, isolation of Sal-resistant mutants. (C) Representative data, PCR-amplification of rpoC (left) and rpoB (right) genes.
Figure 7:
FIG. 7. Crystal structure of *E. coli* RNAP $\sigma^{70}$ holoenzyme in complex with Sal. Panel A shows electron density for Sal (#; $2\sigma F_o - F_c$ difference electron density for *E. coli* RNAP $\sigma^{70}$ holoenzyme with Sal vs. *E. coli* RNAP holoenzyme without Sal). Panel B shows, for comparison, sites of substitutions that confer Sal-resistance (*; see Tables 2-3). In each panel, the RNAP active-center $Mg^{2+}$ ion is illustrated as a sphere (**).
Figure 7:

The results of this research show that Sal inhibits RNA synthesis in vivo (FIG. 2) and show that mutations in RNAP-subunit genes result in Sal-resistance (FIG. 3; Tables 1-3), thereby demonstrating that RNAP is the functional cellular target of Sal. In addition, the results of this research show that transcription inhibition by Sal requires a compact determinant—the "Sal target"—adjacent to and overlapping the RNAP active center and adjacent to but not overlapping the targets of the RNAP inhibitors rifamyins and CBR703 (FIG. 5-; Tables 2-5). The Sal target comprises RNAP β'-subunit residues 690, 697, 738, 748, 758, 763, 775, 779, 780, 782, and 783 and RNAP β subunit residues 561, 569, 665, 675, 677, and 680. Finally, determination of a crystal structure of *E. coli* RNAP in complex with Sal shows that the Sal target is the binding site on RNAP for Sal, and that sites of substitutions conferring Sal-resistance correspond to RNAP residues of RNAP that contact or are close to Sal (FIG. 7).

The Sal target is located adjacent to, and partly overlaps, the RNAP active center (FIGS. 4-7). It is inferred that Sal most likely inhibits RNAP by inhibiting RNAP active-center function.

Most sites of substitutions conferring Sal-resistance involve amino acids that are conserved in RNAP from a broad range of bacterial species (FIG. 4, upper rows in each panel); this is consistent with, and accounts for, the observation that Sal inhibits RNAP from a broad range of bacterial species (4). Nine of the sites of substitutions conferring Sal-resistance—β' residues 690, 697, 738, 775 and 779, and β residues 569, 675, 677, and 680—are not conserved in human RNAP I, RNAP II, and RNAP III (FIG. 4, bottom three rows in each panel); this is consistent with, and accounts for, the observation that Sal does not inhibit human RNAPs (4).

Mapping of substitutions conferring Sal-resistance onto the three-dimensional structure of a transcription elongation complex comprising RNAP, DNA, RNA, and a nucleoside triphosphate (9) indicates that the Sal target does not overlap the RNAP active-center $Mg^{2+}$ ion and does not overlap RNAP residues that interact with the DNA template, the RNA product, and the nucleoside triphosphate substrate. It is inferred Sal most likely inhibits RNAP active-center function allosterically, through effects on RNAP conformation, and not through direct interactions with RNAP residues that mediate bond formation, product binding, and substrate binding.

Figure 4B:
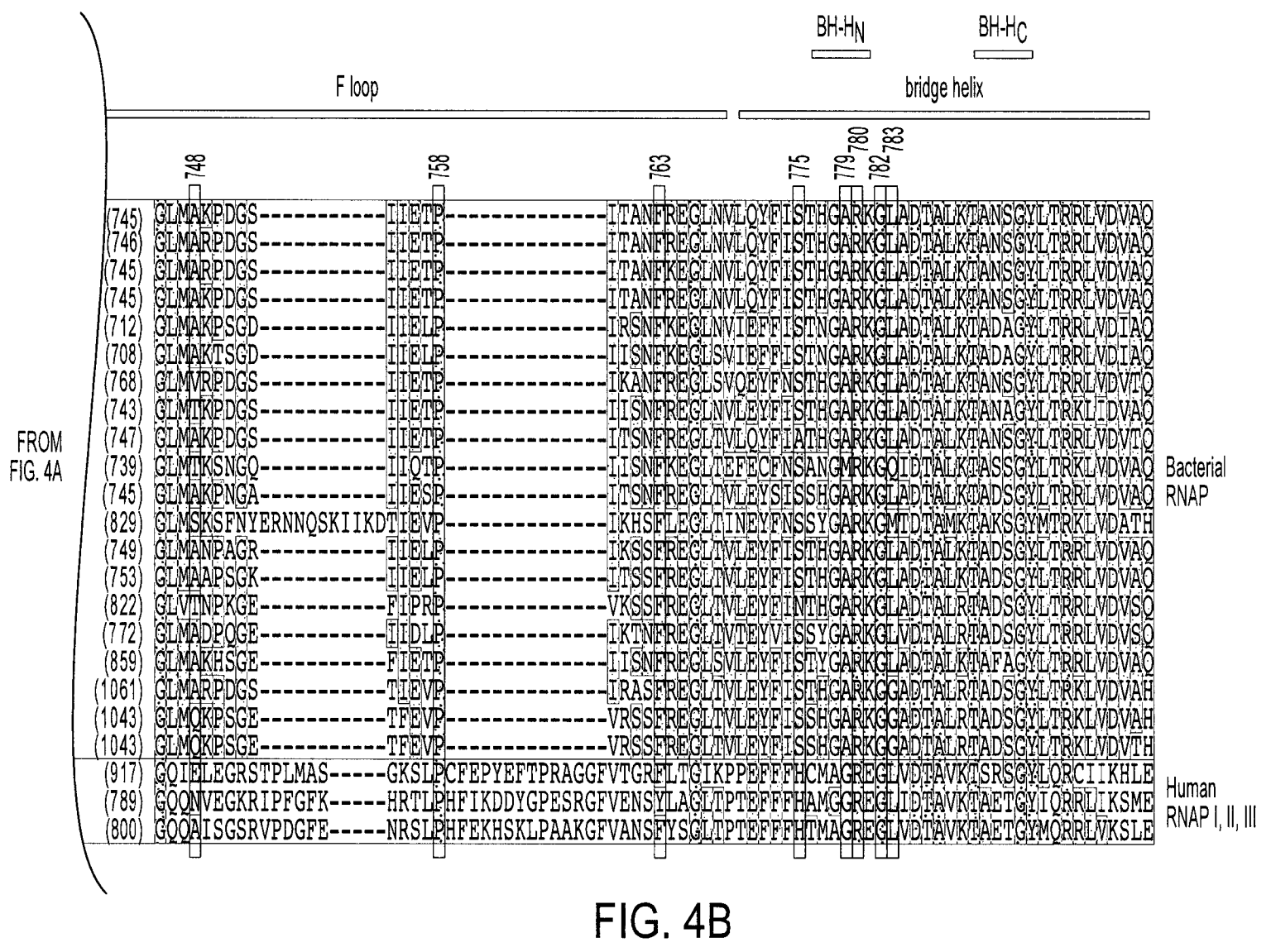

The Sal target overlaps RNAP active-center sub-regions that have been designated as the "β' bridge helix hinge N" (BH-$H_N$), the "β' F loop," the "β link region," and the "β D2 loop" (FIG. 4; active-center sub-region nomenclature as in 18, 19). Fully 20 of the 24 identified substitutions conferring Sal-resistance map to these RNAP active-center sub-regions (FIG. 4; Tables 2-3). The BH-$H_N$ may undergo conformational changes coupled to, and essential for, the nucleotide-addition cycle in RNA synthesis, and the F-loop, and possibly also the link region and the D-2-loop, may coordinate these conformational changes (18, 19). It is inferred herein that Sal most likely inhibits RNAP active-center function by inhibiting BH-$H_N$ hinge-opening and/or hinge-closing.

Sal is the first RNAP inhibitor that has been inferred to function through effects on BH-$H_N$ conformational cycling. Accordingly, Sal will find use as a research tool for dissection of mechanistic and structural aspects of BH-$H_N$ conformational cycling.

Figure 6:
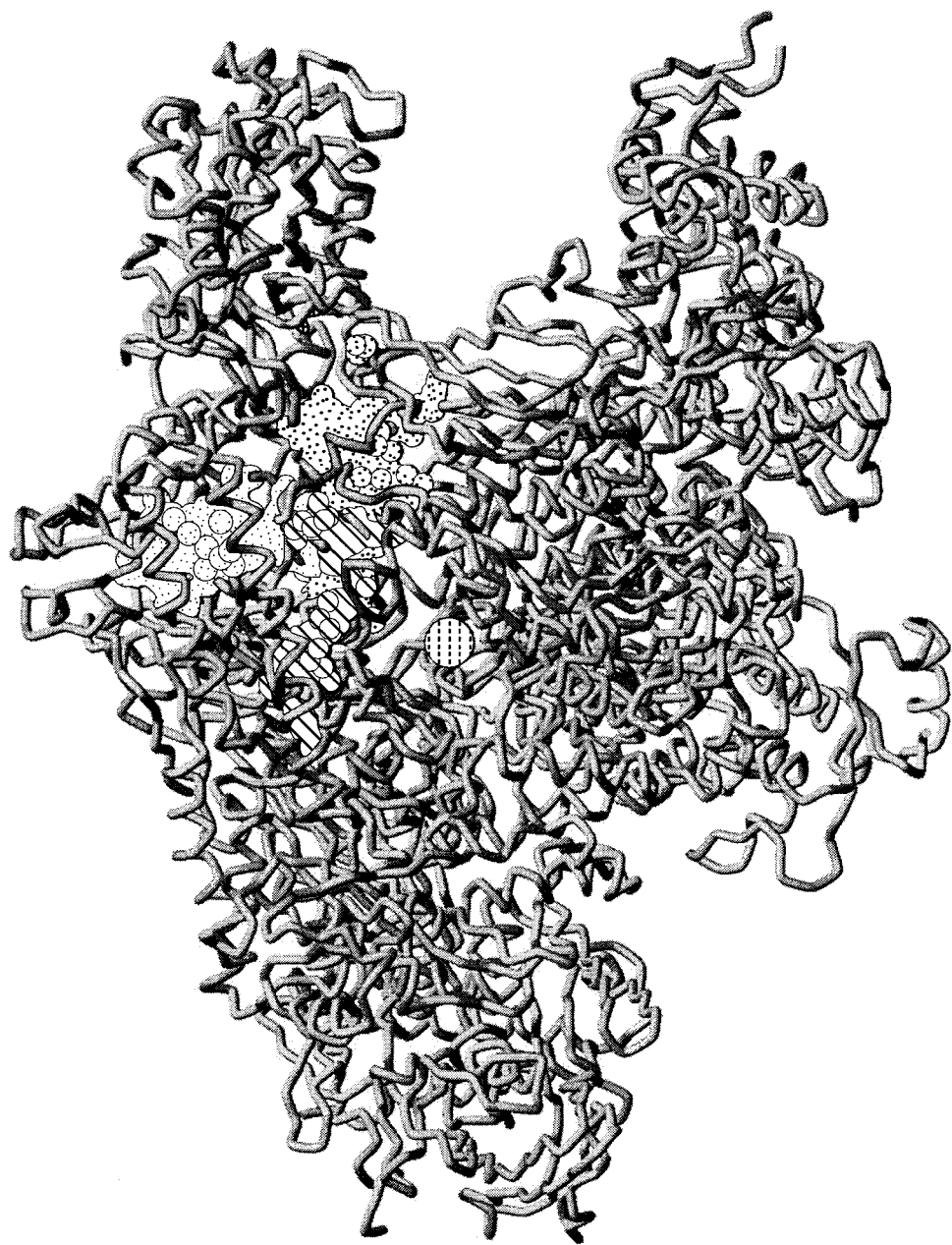
FIG. 6. Sal target: relationship between the Sal target, the rifamycin target, and the CBR703 target. Three-dimensional structure of RNAP showing the Sal target, the rifamycin target, and the CBR703 target. Sites of substitutions that confer Sal-resistance (diagonal lines) (*) (see Tables 2-3), rifamycin-resistance (bold dots) (***) (10-15), and CBR703-resistance (dots) (* * *) (16, 17) are illustrated in space-filling representations. The RNAP active-center $Mg^{2+}$ion is illustrated as a sphere with dotted diagonal lines (**).

Relationship Between the Sal Target and the Rifamycin Target. The Sal target is located adjacent to, but does not overlap, the target of the rifamycin antibacterial agents (e.g., rifampin, rifapentine, rifabutin, and rifalazil), which are RNAP inhibitors in current clinical use in antibacterial therapy (FIG. 6). Consistent with the lack of overlap between the Sal target and the rifamycin target, Sal-resistant mutants are not cross-resistant to the rifamycin rifampin (Table 4), and rifamycin-resistant mutants are not cross-resistant to Sal (Table 5). The absence of overlap and the absence of cross-resistance indicates that it should be possible to co-administer Sal and a rifamycin in order to achieve additive or superadditive antibacterial activities and in order to suppress the emergence of resistance. Consistent with this inference, co-administration of Sal and the rifamycin rifampin results in an extremely low, effectively negligible, spontaneous resistance frequency: $<2\times10^{-11}$ ($<\frac{1}{200}$ the spontaneous resistance frequency of Sal alone; $<\frac{1}{500}$ the spontaneous resistance frequency of rifampin alone; Table 6). This is important in view of the fact that susceptibility to spontaneous resistance is the main limiting factor in the clinical use of rifamycins (15, 21, 22).

Relationship between the Sal target and the CBR703 target. The Sal target also is located adjacent to, but does not overlap, the target of CBR703, an RNAP inhibitor under investigation for clinical use in antibacterial therapy (FIG. 6). Consistent with the lack of overlap between the Sal target and the CBR703 target, Sal-resistant mutants exhibit no cross-resistance to CBR703 (Table 4). In fact, the majority of Sal-resistant mutants exhibit hypersensitivity to CBR703, and half exhibit high-level hypersensitivity to CBR703 (i.e., are at least four times more sensitive to CBR703 than the wild-type parent strain; Table 4). The absence of overlap, the absence of cross-resistance, and the presence of hypersensitivity, indicate that it should be possible to co-administer Sal and CBR703 in order to achieve additive or superadditive antibacterial activities and in order to suppress the emergence of resistance. Consistent with this inference, co-administration of Sal and CBR703 results in an extremely low, effectively negligible, spontaneous resistance frequency: $<2\times10^{-11}$ ($<\frac{1}{200}$ the spontaneous resistance frequency of Sal alone; $<\frac{1}{10}$ the spontaneous resistance frequency of CBR703 alone; Table 7).

Results

Sal Inhibits RNA Synthesis in vivo. To determine whether Sal inhibits RNAP in vivo, effects of Sal on RNA synthesis in vivo were assayed, and, as a control, effects of Sal on DNA synthesis in vivo were assayed. Sal was added to cultures of *E. coli* D21f2tolC growing in media containing either a radioactively labeled RNA-synthesis precursor ([$^{14}$C]-uracil) or a radioactively labeled DNA synthesis precursor ([$^{14}$C]-thymidine); aliquots were removed and mixed with trichloroacetic acid (TCA) 0, 5, 10, and 15 min thereafter to lyse cells and precipitate nucleic acids; TCA-precipitated nucleic acids were collected by vacuum filtration; and radioactivity in TCA-precipitated nucleic acids was quantified (FIG. 2A). It was observed that, upon addition of Sal to bacterial cultures, RNA synthesis essentially stopped (FIG. 2B, left panel). The effect was rapid; it was observed at the earliest time point tested (5 min; FIG. 2B, left panel). The effect was specific; addition of Sal to bacterial cultures had no effect on DNA synthesis (FIG. 2B, right panel). It is concluded that Sal inhibits RNA synthesis in vivo, and it is inferred that Sal inhibits RNAP in vivo.

Sal-Resistant Mutants Map to RNAP-Subunit Genes. To determine whether Sal kills bacteria by inhibiting RNAP, spontaneous Sal-resistant mutants were isolated, and genes for RNAP subunits in Sal-resistant mutants were PCR-amplified and sequenced (FIG. 3A). Spontaneous Sal-resistant mutants were isolated by plating high-density cultures of *E. coli* D21f2tolC (~$3\times10^9$ cells per plate) on agar containing Sal and identifying rare resistant colonies (FIG. 3B). For each Sal-resistant mutant, genomic DNA was prepared, and the genes for the largest RNAP subunit and the second-largest RNAP subunit—rpoC encoding RNAP β' subunit and rpoB encoding RNAP β subunit were PCR-amplified and sequenced (FIG. 3C).

Spontaneous Sal-resistant mutants were isolated with a frequency of ~$4\times10^{-9}$ (Table 1). A total of 39 Sal-resistant mutants were isolated, PCR-amplified, and sequenced (Table 1). Strikingly, one hundred percent (39 of 39) of sequenced Sal-resistant mutants were found to contain mutations in genes for RNAP subunits: 31 were found to contain single mutations in rpoC, 1 was found to contain a double mutation in rpoC, and 7 were found to contain single mutations in rpoB (Table 1). It is concluded that a single substitution in an RNAP-subunit gene, either rpoC or rpoB, is sufficient to confer Sal-resistance, and it is inferred that RNAP is the functional cellular target for Sal.

TABLE 1

Sal-resistant mutants: summary statistics

| | |
|---|---|
| frequency of spontaneous mutation to Sal-resistance | ~4 × 10$^{-9}$ |
| number of Sal-resistant isolates | 39 |
| number of Sal-resistant isolates containing single-substitution mutations in rpoC | 31 |
| number of Sal-resistant isolates containing multiple-substitution mutations in rpoC | 1 |
| number of Sal-resistant isolates containing single-substitution mutations in rpoB | 7 |
| number of Sal-resistant isolates containing multiple-substitution mutations in rpoB | 0 |
| percentage of Sal-resistant isolates containing mutations in RNAP-subunit genes | 100 |

Sal-Resistant Mutants Define Residues of RNAP Important for Function of Sal. A total of 20 different substitutions conferring Sal-resistance were identified (Table 2). Substitutions were obtained at 11 sites in RNAP β' subunit (residues 690, 697, 738, 748, 758, 763, 779, 780, 782, and 783) and at 3 sites in RNAP β subunit (residues 569, 675, and 677) (Table 2; FIG. 4).

Seven additional Sal-resistant mutants were isolated following mutagenesis of rpoC and rpoB. Substitutions conferring Sal-resistance were obtained at 3 sites in RNAP β subunit (residues 561, 665, and 680) and 3 sites in RNA β' subunit (residues 758, 780, and 782) (Table 3; FIG. 4).

Figure 5:
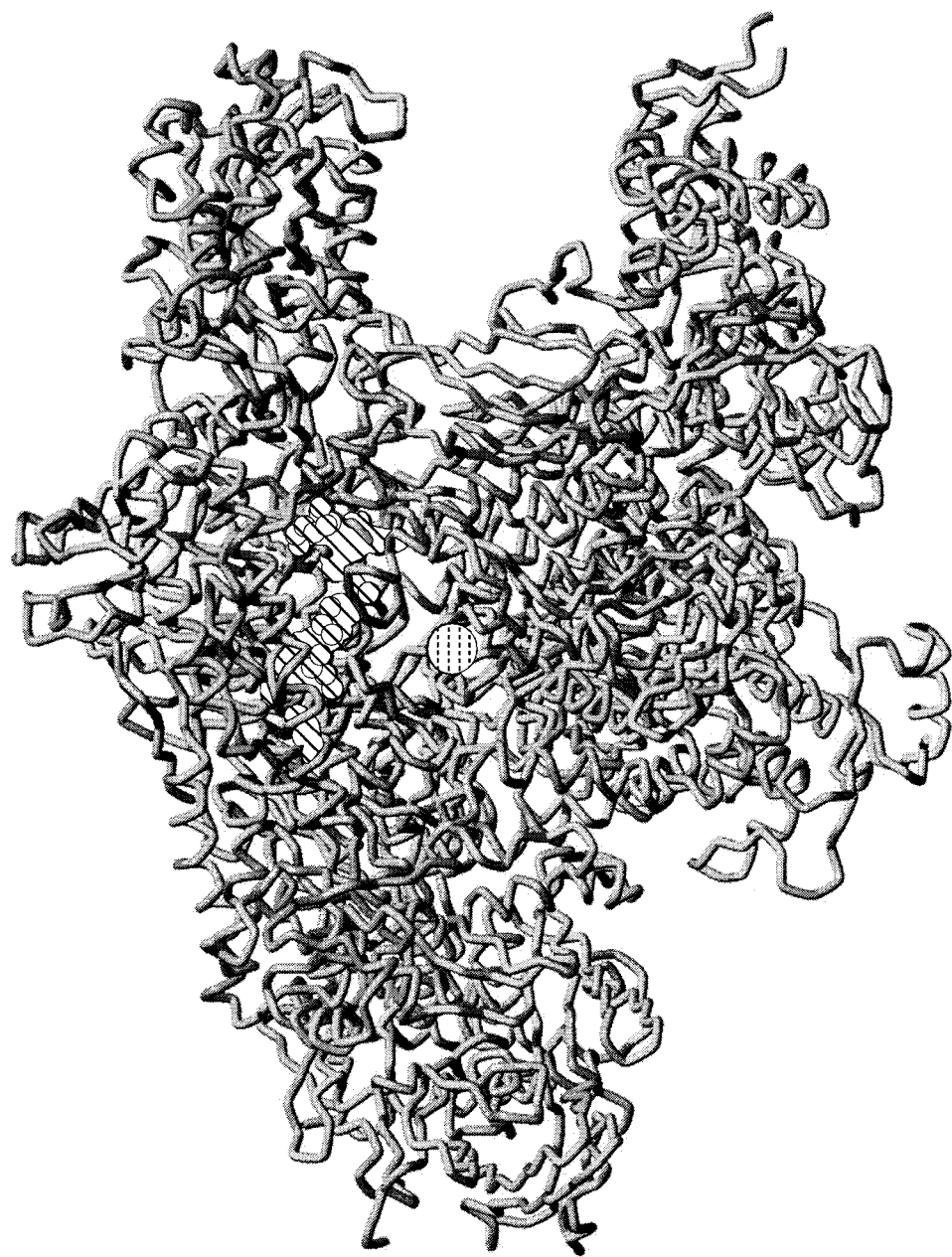
FIG. 5. Sal target: location in the three-dimensional structure of RNAP. Three-dimensional structure of RNAP showing the Sal target. RNAP is illustrated in a ribbon representation. Sites of substitutions that confer Sal-resistance (see Tables 2-3) are illustrated in a space-filling representation. (*) The RNAP active-center $Mg^{2+}$ion is illustrated as a sphere (**). The structure shown is a crystal structure of *T. thermophilus* RNAP holoenzyme (8;β'-subunit non-conserved region and a subunit omitted for clarity); correspondences between residues of *E. coli* RNAP and *T. thermophilus* RNAP are based on amino acid sequence alignments (see FIG. 4).

In the three-dimensional structure of RNAP, the sites of substitutions conferring Sal-resistance formed a tight cluster (the "Sal target"; see FIG. 5). The identified Sal target was located immediately adjacent to, and partly overlapped, the RNAP active center. The Sal target was located adjacent to, but did not overlap, the targets of RNAP inhibitors in current use in antibacterial therapy, rifamycins (see FIG. 6; and 10-15), and the target of an RNAP inhibitor under investigation for use in antibacterial therapy, CBR703 (see FIG. 6; and 16, 17).

The dimensions of the identified Sal target were ~35 Å×~18 Å×~12 Å, and thus the identified Sal target was sufficiently large to be able to encompass Sal (~16 Å×~12 Å×~10 Å). Based on the resistance properties and the size of the Sal target, it was inferred that the Sal target most likely was the binding site for Sal on RNAP.

TABLE 2

Spontaneous Sal-resistant mutants: sequences and properties

| amino acid substitution | number of independent isolates | resistance level (MIC/MIC$_{wild-type}$)[a] |
|---|---|---|
| rpoC (RNAP β' subunit) | | |
| 690 Asn→Asp | 2 | 16 |
| 697 Met→Val[b] | 3 | >16 |
| 738 Arg→Cys | 2 | >16 |
| 738 Arg→His | 1 | >16 |
| 738 Arg→Pro | 2 | >16 |
| 738 Arg→Ser | 1 | >16 |
| 748 Ala→Glu | 2 | 16 |
| 758 Pro→Ser | 1 | 16 |
| 763 Phe→Cys | 4 | 16 |
| 775 Ser→Ala | 1 | 8 |
| 779 Ala→Thr | 2 | >16 |
| 779 Ala→Val | 5 | >16 |
| 780 Arg→Cys | 2 | >16 |
| 782 Gly→Ala | 2 | |
| 782 Gly→Cys | 1 | |
| 783 Leu→Arg | 1 | >16 |
| rpoB (RNAP β subunit) | | |
| 569 Ile→Ser | 2 | >16 |
| 675 Asp→Ala | 2 | >16 |
| 677 Asn→His | 1 | >16 |
| 677 Asn→Lys | 2 | >16 |

[a]MIC with wild-type rpoC and wild-type rpoB was 0.024 µg/ml.
[b]One isolate was a double-substitution mutant: 697 Met→Val; 1054 Thr→Ala.

TABLE 3

Induced Sal-resistant mutants: sequences and properties

| amino acid substitution | number of independent isolates | resistance level (MIC/MIC$_{wild-type}$)[a] |
|---|---|---|
| rpoC (RNAP β' subunit) | | |
| 758 Pro→Thr | 1 | 4 |
| 780 Arg→Cys | 2 | 8 |
| 782 Gly→Cys | 1 | 8 |
| rpoB (RNAP β subunit) | | |
| 561 Ile→Ser | 1 | 2 |
| 665 Ala→Glu | 1 | 8 |
| 680 Leu→Met | 1 | 4 |

[a]Assayed as D21f2tolC pRL663 and D21f2tolC pRL706 derivatives; MIC with wild-type rpoC and wild-type rpoB was 0.098 µg/ml.
[b]One isolate was a double-substitution mutant: 697 Met→Val; 1054 Thr→Ala.

Crystal Structures Confirm Identification of Residues of RNAP Important for Function of Sal. Crystal structures were determined for E. coli RNAP σ$^{70}$ holoenzyme in the presence of Sal (resolution=4.2 Å) and in the absence of Sal (resolution=4.0 Å) (FIG. 7). Comparison of electron density maps for E. coli RNAP σ$^{70}$ holoenzyme in the presence of Sal to E. coli RNAP σ$^{70}$ holoenzyme in the absence of Sal revealed unambiguous difference density attributable to Sal (FIG. 7A). The difference density was located in the Sal target (FIG. 7A) and was in contact with or close to sites of substitutions conferring Sal resistance are obtained (FIG. 7B). The results establish that the Sal target is the binding site on RNAP for Sal, and that sites of substitutions conferring Sal-resistance correspond to RNAP residues of RNAP that contact or are close to Sal.

Resistance Levels of Sal-Resistant Mutants. Resistance to Sal was quantified using broth microdilution assays. All analyzed mutants exhibited at least 2-fold resistance to Sal (Tables 2, 3). Thirteen mutants exhibited >16-fold resistance to Sal.

Cross-Resistance Levels of Sal-Resistant Mutants. Cross-resistance to previously characterized small-molecule inhibitors of RNAP was quantified by use of broth microdilution assays. The Sal-resistant mutants exhibited no cross-resistance with rifampin and no cross-resistance with CBR703 (Table 4). Indeed, two Sal-resistant mutants exhibited moderate, 2-fold, hypersensitivity to rifampin, and ten Sal-resistant mutants exhibited moderate to high-level, 2-fold to >4-fold, hypersensitivity to CBR703 (mutants with resistance levels<1 in Table 4).

TABLE 4

Sal-resistant mutants: absence of cross-resistance to rifampin and CBR703

| amino acid substitution | cross-resistance level (MIC/MIC$_{wild-type}$)[a] | |
|---|---|---|
| | rifampin | CBR703 |
| rpoC (RNAP β' subunit) | | |
| 690 Asn→Asp | 1 | ≤0.25[b] |
| 697 Met→Val | 0.5 | 0.5 |
| 738 Arg→Cys | 1 | ≤0.25 |
| 738 Arg→Pro | 1 | ≤0.25 |
| 738 Arg→Ser | 1 | 1 |
| 748 Ala→Glu | 1 | ≤0.25 |
| 763 Phe→Cys | 1 | ≤0.25 |
| 779 Ala→Thr | 1 | 1 |
| 779 Ala→Val | 1 | ≤0.25 |
| 780 Arg→Cys | 1 | 0.5 |
| 782 Gly→Ala | | |
| 782 Gly→Cys | | |
| rpoB (RNAP β subunit) | | |
| 569 Ile→Ser | 1 | 1 |
| 675 Asp→Ala | 0.5 | ≤0.25 |
| 677 Asn→His | 1 | 1 |
| 677 Asn→Lys | 1 | ≤0.25 |

[a]MIC with wild-type rpoC and wild-type rpoB was 0.098 μg/ml for rifampin and 6.25 μg/ml for CBR703.
[b]Values <1 indicate that the substitution conferred hypersensitivity to the inhibitor.

Cross-Resistance Levels of Rifamycin-Resistant Mutants. More than 70% of clinical isolates of rifamycin-resistant *Mycobacterium tuberculosis* contain β Asp516→Val, β His526→Asp, β His526→Tyr, or β Ser531→Leu substitutions (15). Derivatives of *E. coli* D21f2tolC containing the corresponding rifamycin-resistant mutations were obtained from laboratory stocks, and cross-resistance to Sal was assessed by use of broth microdilution assays. The rifamycin-resistant mutants exhibited no cross-resistance to Sal (Table 5).

TABLE 5

Rifampin-resistant mutants: absence of cross-resistance to Sal

| amino acid substitution rpoB (RNAP β subunit) | cross-resistance level (MIC/MIC$_{wild-type}$)[a] |
|---|---|
| 516 Asp→Val | 1 |
| 526 His→Asp | 1 |
| 526 His→Tyr | 1 |
| 531 Ser→Leu | 1 |

[a]MIC with wild-type rpoB is 0.024 μg/ml.

Co-Administration of Sal and Rifampin Reduces Spontaneous Resistance to Undetectable Levels. Spontaneous resistance frequencies were determined by plating *E. coli* D21f2tolC on LB agar (7) containing Sal at 4×MIC, rifampin at 4×MIC, or both, and counting numbers of colonies after 24 h at 37° C. The results in Table 6 show that the spontaneous resistance frequencies for Sal alone, rifampin alone, and Sal co-administered with rifampin were, respectively, $4 \times 10^{-9}$, $1 \times 10^{-8}$, and undetectable ($<2 \times 10^{-11}$).

TABLE 6

Spontaneous resistance frequencies for Sal, rifampin, and co-administered Sal and rifampin

| compound | spontaneous resistance frequency |
|---|---|
| Sal | $4 \times 10^{-9}$ |
| Rif | $1 \times 10^{-8}$ |
| Sal + Rif | $<2 \times 10^{-11}$ |

Co-Administration of Sal and CBR703 Reduces Spontaneous Resistance to Undetectable Levels. Spontaneous resistance frequencies were determined by plating *E. coli* D21f2tolC on LB agar (7) containing Sal at 4×MIC, CBR703 at 4×MIC, or both, and counting numbers of colonies after 24 h at 37° C.

The results in Table 7 show that the spontaneous resistance frequencies for Sal alone, CBR703 alone, and Sal co-administered with CBR703 were, respectively, $4 \times 10^{-9}$, $2 \times 10^{-10}$, and undetectable ($<2 \times 10^{-11}$).

TABLE 7

Spontaneous resistance frequencies for Sal, CBR703, and co-administered Sal and CBR703

| compound | spontaneous resistance frequency |
|---|---|
| Sal | $4 \times 10^{-9}$ |
| CBR703 | $2 \times 10^{-10}$ |
| Sal + CBR703 | $<2 \times 10^{-11}$ |

Materials and Methods

Sal. Sal was isolated as in reference 1.

Measurement of Nucleic Acid Synthesis in vivo. Macromolecular synthesis assays were performed essentially as in reference 5. *Escherichia coli* D21f2tolC (a strain with cell-envelope defects resulting in increased susceptibility to antibiotics, including Sal; 6) was cultured in 10 ml M5T broth (5) at 37° C. with shaking until $OD_{600}$=0.4-0.8, and cultures were diluted with pre-warmed M5T broth to $OD_{600}$=0.167. Aliquots (90 μl) were dispensed into wells of a 96-well plate, were supplemented with 7 μl pre-warmed 6 μCi/ml [$^{14}$C]-uracil or [$^{14}$C]-thymidine, were supplemented with 3 μl 0.048 μg/ml Sal in methanol (yielding a final Sal concentration two times the minimal inhibitory concentration) or 3 μl solvent blank, and were incubated at 37° C. with shaking. At time points 0, 5, 10, and 15 min after the addition of Sal or solvent blank, rows of samples were transferred to a second 96-well plate, containing 100 μl ice-cold 10% trichloroacetic acid (TCA) in each well, and the second plate was incubated on ice. One hour after the final time point, TCA precipitates were collected by filtration onto glass-fibre filters (Filtermat A; Perkin-Elmer, Inc.; pre-rinsed twice with 5% TCA), washed twice with 5% TCA, washed three times with water, and washed twice with 10% ethanol, using a Packard FilterMate 196 cell harvester with an OmniFilter upper head assembly (Perkin-Elmer, Inc.). Filters were dried under a heat lamp, wrapped in a single layer of plastic wrap, and exposed to a phosphorimager screen for 16-18 h. Radioactivity was quantified using a Typhoon Variable Mode Imager and ImageQuant v5 (Molecular Dynamics, Inc.).

Isolation of Sal-Resistant Mutants: Spontaneous Sal-Resistant Mutants. *E. coli* D21f2tolC (6) was cultured to saturation in 5 ml LB broth (7) at 37° C., cultures were centrifuged, and cell pellets (~$3 \times 10^9$ cells) were re-suspended in 50 μl LB broth and plated on LB agar (7) containing 1.2 μg/ml Sal (a concentration four times the minimal concentration required to prevent growth of wild-type cells under these conditions), and incubated 24-48 h at 37° C. Sal-resistant mutants were identified by the ability to form colonies on this medium and were confirmed by re-streaking on the same medium.

Isolation of Sal-Resistant Mutants: Induced Sal-Resistant Mutants. *E. coli* Random mutagenesis of rpoC in plasmid pRL663 and rpoB in plasmid pRL706 was performed as in 24, mutagenenized plasmids were passaged in *E. coli* XL1-Blue (Stratgene, Inc.) as in 24, mutagenized plasmids were introduced by transformation into *E. coli* D21f2tolC as in 24, and transformants (~1×10$^4$ cells) were applied to LB-agar plates containing 1 µg/ml Sal, 200 µg/ml ampicillin, and 1 mM IPTG, and plates were incubated 16-24 h at 37° C. Sal-resistant mutants were identified by the ability to form colonies on this medium and were confirmed by re-streaking on the same medium.

PCR-amplification and sequencing of RNAP-subunit genes of Sal-resistant mutants. For spontaneous Sal-resistant mutants, rpoC and rpoB genese were PCR-amplified and sequenced as follows: Genomic DNA was isolated using the Wizard Genomic DNA Purification Kit (Promega, Inc.; procedures as specified by the manufacturer) and was quantified by measurement of UV-absorbance (procedures as in 7). The rpoC gene and the rpoB gene were PCR-amplified in reactions containing 0.2 µg genomic DNA, 0.4 µM forward and reverse oligonucleotide primers (5'-AGGTCACTGCT-GTCGGGTTAAAACC- 3' (SEQ ID NO:1) and 5'-TGA-CAAATGCTCTT TCCCTAAACTCC-3' (SEQ ID NO:2) for rpoC; 5'-GTTGCACAAACTGTCCGCTCAATGG-3' (SEQ ID NO:3) and 5'-TCGGAGTTAGCACAATCCGCTGC-3' (SEQ ID NO:4) for rpoB), 5 U Taq DNA polymerase (Genscript, Inc.), and 800 µM dNTP mix (Agilent/Stratagene, Inc.) (initial denaturation step of 5 min at 94° C.; 30 cycles of 30 s at 94° C., 45 s at 55° C., and 4.5 min at 72° C.; final extension step of 10 min at 72° C.). PCR products containing the rpoC gene (4.3 kB) or the rpoB gene (4.1 kB) were isolated by electrophoresis on 0.8% agarose (procedures as in 7), extracted from gel slices using the Gel/PCR DNA Fragments Extraction Kit (IBI Scientific, Inc.; procedures as specified by the manufacturer), and submitted to High-Throughput Sequencing Solutions (Seattle WA) for sequencing (Sanger sequencing; eight sequencing primers per gene).

For each induced Sal-resistant mutants, plasmid DNA was isolated and submitted to High-Throughput Sequencing Solutions (Seattle Wash.) for sequencing (Sanger sequencing; eight sequencing primers per gene).

Quantitation of Resistance to Sal. Resistance to Sal was quantified by performing broth microdilution assays. Single colonies were inoculated into 3 ml LB broth, and incubated 3-6 h at 37° C. with shaking. Diluted aliquots (2×10$^4$ cells in 98 µl LB broth; concentrations determined using OD$_{600}$=1 for 10$^9$ cells) were dispensed into wells of a 96-well plate, were supplemented with 2 µl of a 2-fold dilution series of Sal in methanol (final concentrations of 1.56, 0.390, 0.195, 0.0975, 0.0488, 0.0244, 0.0122, and 0.00609 µg/ml) or 2 µl of a solvent blank, and were incubated 16 h at 37° C. with shaking. The minimum inhibitory concentration (MIC) was defined as the lowest tested concentration of Sal that inhibited bacterial growth by 95%.

Quantitation of Cross-Resistance to Rifampin and CBR703. Cross-resistance levels were determined analogously to resistance levels, using 0.12-0.78 µg/ml of rifampin (Sigma, Inc.) and 0.39-25 µg/ml of CBR703 (Maybridge, Inc.).

Molecular Modeling. Sites of substitutions conferring Sal-resistance were mapped onto a crystal structure of *Thermus thermophilus* RNAP holoenzyme (8; PDB accession code 1L9U) and a crystal structure of the *T. thermophilus* transcription elongation complex (RNAP in complex with DNA, RNA, and a nucleoside triphosphate; 9; PDB accession code 2O5J). Correspondences between residues of *E. coli* RNAP and *T. thermophilus* RNAP were based on amino acid sequence alignments (25; FIG. 4).

REFERENCES

1. Trischman, J., Tapiolas, D., Jensen, P., Dwight, R., Fenical, W., McKee, T., Ireland, C., Stout, T., and Clardy, J (1994) Salinamides A and B: anti-inflammatory depsipeptides from a marine streptomycete. *J. Am. Chem. Soc.,* 1994, 116, 757-758.
2. Moore, B., Trischman, J., Dieter Seng, D., Kho, D., Jensen, P., and Fenical, W. (1999) Salinamides: antiinflammatory depsipeptides from a marine streptomycete. *J. Org. Chem.,* 64, 1145-1150.
3. Moore, B. and Seng, D. (1998) Biosynthesis of the bicyclic depsipeptide salinamide A in *Streptomyces* sp. CNB-091: origin of the carbons. *Tetrahedron Lett.* 39, 3915-3918.
4. Miao, S., Anstee, M., LaMarco, K., Matthew, J., Huang, L., and Brasseur, M. (1997) Inhibition of bacterial RNA polymerases: peptide metabolites from the cultures of *Streptomyces* sp. *J. Nat. Prod.* 60, 858-861.
5. King, A. and Wu, L. (2009) Macromolecular synthesis and membrane perturbation assays for mechanisms of action studies of antimicrobial agents. *Curr. Protoc. Pharmacol.* 47:13A.7.1-13A.7.23.
6. Fralick, J., and Burns-Keliher, L. (1994). Additive effect of to/C and rfa mutations on the hydrophobic barrier of the outer membrane of *E. coli* K-12. *J. Bacteriol.* 176, 6404-6406.
7. Sambrook, J., and Russell, D. (2001). *Molecular Cloning: A Laboratory Manual* (Cold Spring Harbor, N.Y., Cold Spring Harbor Laboratory).
8. Vassylyev, D., Sekine, S., Laptenko, O., Lee, J., Vassylyeva, M., Borukhov, S., and Yokoyama, S. (2002). Crystal structure of a bacterial RNA polymerase holoenzyme at 2.6 Å resolution. *Nature* 417, 712-719.
9. Vassylyev, D., Vassylyeva, M., Zhang, J., Palangat, M., Artsimovitch, I., and Landick, R. (2007). Structural basis for substrate loading in bacterial RNA polymerase. *Nature* 448, 163-168.
10. Ovchinnikov, Y., Monastyrskaya, G., Gubanov, V., Lipkin, V., Sverdlov, E., Kiver, I., Bass, I., Mindlin, S., Danilevskaya, O., and Khesin, R. (1981). Primary structure of *Escherichia coli* RNA polymerase nucleotide substitution in the β subunit gene of the rifampicin resistant rpoB255 mutant. *Mol. Gen. Genet.* 184, 536-538.
11. Ovchinnikov, Y., Monastyrskaya, G., Guriev, S., Kalinina, N., Sverdlov, E., Gragerov, A., Bass, I., Kiver, I., Moiseyeva, E., Igumnov, V., et al. (1983). RNA polymerase rifampicin resistance mutations in *Escherichia coli*: sequence changes and dominance. *Mol. Gen. Genet.* 190, 344-348.
12. Jin, D. J., and Gross, C. (1988). Mapping and sequencing of mutations in the *Escherichia coli* rpoB gene that lead to rifampicin resistance. *J. Mol. Biol.* 202, 45-58.
13. Severinov, K., Soushko, M., Goldfarb, A., and Nikiforov, V. (1993). Rifampicin region revisited: new rifampicin-resistant and streptolydigin-resistant mutants of the β subunit of *Escherichia coli* RNA polymerase. *J. Biol. Chem.* 268, 14820-14825.

14. Campbell, E., Korzheva, N., Mustaev, A., Murakami, K., Nair, S., Goldfarb, A., and Darst, S. (2001). Structural mechanism for rifampicin inhibition of bacterial RNA polymerase. *Cell* 104, 901-912.
15. Ho, M., Hudson, B., Das, K., Arnold, E., and Ebright, R. (2009) Structures of RNA polymerase-antibiotic complexes. *Curr. Opin. Structl. Biol.* 19, 715-723.
16. Artsimovitch, I., Chu, C., Lynch, A., and Landick, R. (2003). A new class of bacterial RNA polymerase inhibitor affects nucleotide addition. *Science* 302, 650-654.
17. Wang, X., Sineva, E., and Ebright, R., personal communication.
18. Weinzierl, R. (2010) The nucleotide addition cycle of RNA polymerase is controlled by two molecular hinges in the Bridge Helix domain. *BMC Biol.* 8:134.
19. Hein, P. and Landick, R. (2010) The bridge helix coordinates movements of modules in RNA polymerase. *BMC Biol.* 8:141.
20. Baquero, M.-R., Nilsson, A., Turrientes, M., Sandvang, D., Galán, J. C., Martínez, J. L., Frimodt-Møller, N., Baquero, F., and Andersson, D. (2004) Polymorphic mutation frequencies in *Escherichia coli*. *J. Bacteriol.*, 186, 5538-5542.
21. Chopra, I. (2007). Bacterial RNA polymerase: a promising target for the discovery of new antimicrobial agents. *Curr. Opin. Investig. Drugs* 8, 600-607.22. Villain-Guillot, P., Bastide, L., Gualtieri, M. & Leonetti, J. (2007) Progress in targeting bacterial transcription. *Drug Discov. Today* 12, 200-208.23. Tan, L. and Ma, D. (2008) Total synthesis of salinamide A: a potent anti-inflammatory bicyclic depsipeptide. *Angew. Chem. Int. Ed.* 47, 3614-3617.
24. Mukhopadhyay, J., Das, K., Ismail, S., Koppstein, D., Jang, M., Hudson, B., Sarafianos, S., Tuske, S., Patel, J., Jansen, R., Irschik, H., Arnold, E. & Ebright, R. (2008) The RNA polymerase "switch region" is a target for inhibitors. *Cell* 135, 295-307.
25. Lane, W. & Darst, S. (2010) Molecular evolution of multisubunit RNA polymerases: sequence analysis *J. Mol. Biol.* 395, 671-85.

All publications cited herein are incorporated herein by reference. While in this application certain embodiments of invention have been described, and many details have been set forth for purposes of illustration, it will be apparent to those skilled in the art that certain of the details described herein may be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not pose a limitation on the scope of the invention unless otherwise specifically recited in the claims. No language in the specification should be construed as indicating that any non-claimed element as essential to the practice of the invention.

What is claimed is:

1. A method for identifying an agent that binds to a bacterial ribonucleic acid polymerase (RNAP) bridge-helix cap target in a first entity, comprising the steps of:
   (a) preparing a reaction solution including the agent to be tested and a first entity including a bacterial RNAP bridge-helix cap target, wherein the bacterial RNAP bridge-helix cap target comprises residues corresponding to, or alignable with, residues 561, 569, 665, 675, 677, and 680 of the β subunit or residues 690, 697, 758, and 763 of the β' subunit of RNA polymerase from *Escherichia coli*; and
   (b) detecting at least one of the presence, extent, concentration-dependence, or kinetics of binding of the agent to the bridge-helix cap target, wherein the agent is not salinamide A.

2. The method of claim 1, wherein the first entity is a bacterial RNAP.

3. The method of claim 1, wherein the first entity is *Escherichia coli* RNAP.

4. The method of claim 1, wherein the first entity is *Bacillus subtilis* RNAP.

5. The method of claim 1, further comprising the step of: assessing at least one of the presence, extent, concentration-dependence, or kinetics of binding of the agent to a second entity that contains a derivative of a bacterial RNAP bridge-helix cap target having at least one substitution, insertion, or deletion.

6. The method of claim 5, wherein the second entity is a derivative of *Escherichia coli* RNAP.

7. The method of claim 5, wherein the second entity is a derivative of *Bacillus subtilis* RNAP.

8. A method for identifying an agent that exhibits antibacterial activity by binding to a bacterial ribonucleic acid polymerase (RNAP) bridge-helix cap target, comprising:
   (a) preparing a reaction mixture comprising the agent to be tested and a first bacterium containing a bacterial RNAP containing a bacterial RNAP bridge-helix cap target, wherein the bacterial RNAP bridge-helix cap target comprises residues corresponding to, or alignable with, residues 561, 569, 665, 675, 677, and 680 of the β subunit or residues 690, 697, 758, and 763 of the β' subunit of RNA polymerase from *Escherichia coli*; and
   (b) detecting inhibition of at least one of viability of the bacterium and growth of the bacterium, wherein inhibition involves binding of the agent to the bacterial RNAP bridge-helix cap target, and wherein the agent is not salinamide A.

9. The method of claim 8, wherein the first bacterium is *Escherichia coli*.

10. The method of claim 8, wherein the first bacterium is a tolC strain of *Escherichia coli*.

11. The method of claim 8, wherein the first bacterium is a tolC rfa strain of *Escherichia coli*.

12. The method of claim 8, wherein the first bacterium is *Bacillus subtilis*.

13. The method of claim 8, further comprising the step of: assessing inhibition by the agent of at least one of viability of a second bacterium and growth of a second bacterium, said second bacterium containing a derivative of a bacterial RNAP containing a bacterial RNAP bridge-helix cap target having at least one substitution, insertion, or deletion.

14. The method of claim 13, wherein the second bacterium is a derivative of *Escherichia coli*.

15. The method of claim 13, wherein the second bacterium is a derivative of a tolC strain of *Escherichia coli*.

16. The method of claim 13, wherein the second bacterium is a derivative of a tolC rfa strain of *Escherichia coli*.

17. The method of claim 13, wherein the second bacterium is a derivative of *Bacillus subtilis*.

18. The method of claim 13, wherein antibacterial activity against the first bacterium and antibacterial activity against the second bacterium are assessed sequentially.

19. The method of claim 13, wherein antibacterial activity against the first bacterium and antibacterial activity against the second bacterium are assessed simultaneously.

* * * * *

SEQUENCE LISTING

```
<160> NUMBER OF SEQ ID NOS: 119

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aggtcactgc tgtcgggtta aaacc                                              25

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgacaaatgc tctttcccta aactcc                                             26

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 3
gttgcacaaa ctgtccgctc aatgg     25

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcggagttag cacaatccgc tgc     23

<210> SEQ ID NO 5
<211> LENGTH: 14
<212> TYPE: PRT
<213> ORGANISM: Escherichia coli

<400> SEQUENCE: 5

Ala Ala Ala Asn Asp Arg Val Ser Lys Ala Met Met Asp Asn
1               5                   10

<210> SEQ ID NO 6
<211> LENGTH: 7
<212> TYPE: PRT
<213> ORGANISM: Escherichia coli

<400> SEQUENCE: 6

Ala Gln Ile Arg Gln Leu Ala
1               5

<210> SEQ ID NO 7
<211> LENGTH: 61
<212> TYPE: PRT
<213> ORGANISM: Escherichia coli

<400> SEQUENCE: 7

Gly Leu Met Ala Lys Pro Asp Gly Ser Ile Ile Glu Thr Pro Ile Thr
1               5                   10                  15

Ala Asn Phe Arg Glu Gly Leu Asn Val Leu Gln Tyr Phe Ile Ser Thr
            20                  25                  30

His Gly Ala Arg Lys Gly Leu Ala Asp Thr Ala Leu Lys Thr Ala Asn
        35                  40                  45

Ser Gly Tyr Leu Thr Arg Arg Leu Val Asp Val Ala Gln
    50                  55                  60

<210> SEQ ID NO 8
<211> LENGTH: 14
<212> TYPE: PRT
<213> ORGANISM: Haemophilus influenzae

<400> SEQUENCE: 8

Ala Ala Ala Asn Glu Arg Val Ala Lys Ala Met Met Glu Asn
1               5                   10

<210> SEQ ID NO 9
<211> LENGTH: 7
<212> TYPE: PRT
<213> ORGANISM: Haemophilus influenzae

<400> SEQUENCE: 9

Ala Gln Ile Arg Gln Leu Ala
1               5

<210> SEQ ID NO 10
<211> LENGTH: 61
<212> TYPE: PRT
<213> ORGANISM: Haemophilus influenzae

<400> SEQUENCE: 10

Gly Leu Met Ala Arg Pro Asp Gly Ser Ile Ile Glu Thr Pro Ile Thr
1               5                   10                  15

Ala Asn Phe Arg Glu Gly Leu Asn Val Leu Gln Tyr Phe Ile Ser Thr
            20                  25                  30

His Gly Ala Arg Lys Gly Leu Ala Asp Thr Ala Leu Lys Thr Ala Asn
        35                  40                  45

Ser Gly Tyr Leu Thr Arg Arg Leu Val Asp Val Ala Gln
    50                  55                  60

<210> SEQ ID NO 11
<211> LENGTH: 14
<212> TYPE: PRT
<213> ORGANISM: Vibrio cholerae

<400> SEQUENCE: 11

Ala Ser Thr Asn Asp Arg Val Lys Ala Met Met Glu Asn
1               5                   10

<210> SEQ ID NO 12
<211> LENGTH: 7
<212> TYPE: PRT
<213> ORGANISM: Vibrio cholerae

<400> SEQUENCE: 12

Ala Gln Ile Arg Gln Leu Ala
1               5

<210> SEQ ID NO 13
<211> LENGTH: 61
<212> TYPE: PRT
<213> ORGANISM: Vibrio cholerae

<400> SEQUENCE: 13

Gly Leu Met Ala Arg Pro Asp Gly Ser Ile Ile Glu Thr Pro Ile Thr
1               5                   10                  15

Ala Asn Phe Lys Glu Gly Leu Asn Val Leu Gln Tyr Phe Ile Ser Thr
            20                  25                  30

His Gly Ala Arg Lys Gly Leu Ala Asp Thr Ala Leu Lys Thr Ala Asn
        35                  40                  45

Ser Gly Tyr Leu Thr Arg Arg Leu Val Asp Val Ala Gln
    50                  55                  60

<210> SEQ ID NO 14
<211> LENGTH: 14
<212> TYPE: PRT
<213> ORGANISM: Pseudomonas aeruginosa

<400> SEQUENCE: 14

Ser Lys Ala Asn Asp Glu Val Ser Lys Ala Met Met Ala Asn
1               5                   10

<210> SEQ ID NO 15

```
<211> LENGTH: 7
<212> TYPE: PRT
<213> ORGANISM: Pseudomonas aeruginosa

<400> SEQUENCE: 15

Ala Gln Ile Arg Gln Leu Ala
1               5

<210> SEQ ID NO 16
<211> LENGTH: 61
<212> TYPE: PRT
<213> ORGANISM: Pseudomonas aeruginosa

<400> SEQUENCE: 16

Gly Leu Met Ala Lys Pro Asp Gly Ser Ile Ile Glu Thr Pro Ile Thr
1               5                   10                  15

Ala Asn Phe Arg Glu Gly Leu Asn Val Leu Gln Tyr Phe Ile Ser Thr
            20                  25                  30

His Gly Ala Arg Lys Gly Leu Ala Asp Thr Ala Leu Lys Thr Ala Asn
        35                  40                  45

Ser Gly Tyr Leu Thr Arg Arg Leu Val Asp Val Ala Gln
    50                  55                  60

<210> SEQ ID NO 17
<211> LENGTH: 14
<212> TYPE: PRT
<213> ORGANISM: Treponema pallidum

<400> SEQUENCE: 17

Ser Lys Thr Ser Glu Glu Leu Thr Ser Leu Met Met Glu Thr
1               5                   10

<210> SEQ ID NO 18
<211> LENGTH: 7
<212> TYPE: PRT
<213> ORGANISM: Treponema pallidum

<400> SEQUENCE: 18

Asn Gln Ile Arg Gln Leu Ala
1               5

<210> SEQ ID NO 19
<211> LENGTH: 61
<212> TYPE: PRT
<213> ORGANISM: Treponema pallidum

<400> SEQUENCE: 19

Gly Leu Met Ala Lys Pro Ser Gly Asp Ile Ile Glu Leu Pro Ile Arg
1               5                   10                  15

Ser Asn Phe Lys Glu Gly Leu Asn Val Ile Glu Phe Phe Ile Ser Thr
            20                  25                  30

Asn Gly Ala Arg Lys Gly Leu Ala Asp Thr Ala Leu Lys Thr Ala Asp
        35                  40                  45

Ala Gly Tyr Leu Thr Arg Arg Leu Val Asp Ile Ala Gln
    50                  55                  60

<210> SEQ ID NO 20
<211> LENGTH: 14
<212> TYPE: PRT
<213> ORGANISM: Borrelia burgdorferi

<400> SEQUENCE: 20
```

```
Leu Lys Thr Asn Glu Glu Leu Thr Asn Lys Met Met Glu Ile
1               5                   10
```

<210> SEQ ID NO 21
<211> LENGTH: 7
<212> TYPE: PRT
<213> ORGANISM: Borrelia burgdorferi

<400> SEQUENCE: 21

```
Asn Gln Ile Arg Gln Leu Ala
1               5
```

<210> SEQ ID NO 22
<211> LENGTH: 61
<212> TYPE: PRT
<213> ORGANISM: Borrelia burgdorferi

<400> SEQUENCE: 22

```
Gly Leu Met Ala Lys Thr Ser Gly Asp Ile Ile Glu Leu Pro Ile Ile
1               5                   10                  15

Ser Asn Phe Lys Glu Gly Leu Ser Val Ile Glu Phe Phe Ile Ser Thr
                20                  25                  30

Asn Gly Ala Arg Lys Gly Leu Ala Asp Thr Ala Leu Lys Thr Ala Asp
            35                  40                  45

Ala Gly Tyr Leu Thr Arg Arg Leu Val Asp Ile Ala Gln
        50                  55                  60
```

<210> SEQ ID NO 23
<211> LENGTH: 14
<212> TYPE: PRT
<213> ORGANISM: Xylella fastidiosa

<400> SEQUENCE: 23

```
Ser Arg Thr Asn Glu Arg Ile Ala Lys Ala Met Met Asp Thr
1               5                   10
```

<210> TYPE: PRT
<213> ORGANISM: Campylobacter jejuni

<400> SEQUENCE: 26

Lys Ser Thr Asn Asn Val Leu Ser Lys Glu Met Met Lys Leu
1               5                   10

<210> SEQ ID NO 27
<211> LENGTH: 7
<212> TYPE: PRT
<213> ORGANISM: Campylobacter jejuni

<400> SEQUENCE: 27

Ala Gln Ile Ser Gln Leu Ala
1               5

<210> SEQ ID NO 28
<211> LENGTH: 61
<212> TYPE: PRT
<213> ORGANISM: Campylobacter jejuni

<400> SEQUENCE: 28

Gly Leu Met Thr Lys Pro Asp Gly Ser Ile Ile Glu Thr Pro Ile Ile
1               5                   10                  15

Ser Asn Phe Arg Glu Gly Leu Asn Val Leu Glu Tyr Phe Ile Ser Thr
                20                  25                  30

His Gly Ala Arg Lys Gly Leu Ala Asp Thr Ala Leu Lys Thr Ala Asn
            35                  40                  45

Ala Gly Tyr Leu Thr Arg Lys Leu Ile Asp Val Ala Gln
        50                  55                  60

<210> SEQ ID NO 29
<211> LENGTH: 14
<212> TYPE: PRT
<213> ORGANISM: Neisseria meningitidis

<400> SEQUENCE: 29

Gly Arg Ala Gly Asp Lys Ile Ala Lys Ala Met Met Asp Asn
1               5                   10

<210> SEQ ID NO 30
<211> LENGTH: 7
<212> TYPE: PRT
<213> ORGANISM: Neisseria meningitidis

<400> SEQUENCE: 30

Ala Gln Ile Lys Gln Leu Ser
1               5

<210> SEQ ID NO 31
<211> LENGTH: 61
<212> TYPE: PRT
<213> ORGANISM: Neisseria meningitidis

<400> SEQUENCE: 31

Gly Leu Met Ala Lys Pro Asp Gly Ser Ile Ile Glu Thr Pro Ile Thr
1               5                   10                  15

Ser Asn Phe Arg Glu Gly Leu Thr Val Leu Gln Tyr Phe Ile Ala Thr
                20                  25                  30

His Gly Ala Arg Lys Gly Leu Ala Asp Thr Ala Leu Lys Thr Ala Asn
            35                  40                  45

Ser Gly Tyr Leu Thr Arg Arg Leu Val Asp Val Thr Gln

<210> SEQ ID NO 32
<211> LENGTH: 14
<212> TYPE: PRT
<213> ORGANISM: Rickettsia prowazekii

<400> SEQUENCE: 32

Ser Arg Cys Thr Asp Arg Val Ala Asn Asp Met Met Lys Glu
1 5 10

<210> SEQ ID NO 33
<211> LENGTH: 7
<212> TYPE: PRT
<213> ORGANISM: Rickettsia prowazekii

<400> SEQUENCE: 33

Gln Gln Ile Lys Gln Leu Gly
1 5

<210> SEQ ID NO 34
<211> LENGTH: 61
<212> TYPE: PRT
<213> ORGANISM: Rickettsia prowazekii

<400> SEQUENCE: 34

Gly Leu Met Thr Lys Ser Asn Gly Gln Ile Ile Gln Thr Pro Ile Ile
1 5 10 15

Ser Asn Phe Lys Glu Gly Leu Thr Glu Phe Glu Cys Phe Asn Ser Ala
20 25 30

Asn Gly Met Arg Lys Gly Gln Ile Asp Thr Ala Leu Lys Thr Ala Ser
35 40 45

Ser Gly Tyr Leu Thr Arg Lys Leu Val Asp Val Ala Gln
50 55 60

<210> SEQ ID NO 35
<211> LENGTH: 14
<212> TYPE: PRT
<213> ORGANISM: Chlamydia trachomatis

<400> SEQUENCE: 35

Thr Glu Val Ser Asp Leu Leu Ser Asn Ala Leu Tyr Ser Glu
1 5 10

<210> SEQ ID NO 36
<211> LENGTH: 7
<212> TYPE: PRT
<213> ORGANISM: Chlamydia trachomatis

<400> SEQUENCE: 36

Ser Gln Leu Lys Gln Leu Gly
1 5

<210> SEQ ID NO 37
<211> LENGTH: 61
<212> TYPE: PRT
<213> ORGANISM: Chlamydia trachomatis

<400> SEQUENCE: 37

Gly Leu Met Ala Lys Pro Asn Gly Ala Ile Ile Glu Ser Pro Ile Thr
1 5 10 15

Ser Asn Phe Arg Glu Gly Leu Thr Val Leu Glu Tyr Ser Ile Ser Ser
20 25 30

```
His Gly Ala Arg Lys Gly Leu Ala Asp Thr Ala Leu Lys Thr Ala Asp
        35                  40                  45

Ser Gly Tyr Leu Thr Arg Arg Leu Val Asp Val Ala Gln
    50                  55                  60
```

<210> SEQ ID NO 38
<211> LENGTH: 14
<212> TYPE: PRT
<213> ORGANISM: Mycoplasma pneumoniae

<400> SEQUENCE: 38

```
Asn Gly Val Lys Glu Lys Val Ser Ser Glu Ile Gln Asp Leu
1               5                   10
```

<210> SEQ ID NO 39
<211> LENGTH: 7
<212> TYPE: PRT
<213> ORGANISM: Mycoplasma pneumoniae

<400> SEQUENCE: 39

```
Ser Asn Phe Thr Gln Leu Phe
1               5
```

<210> SEQ ID NO 40
<211> LENGTH: 72
<212> TYPE: PRT
<213> ORGANISM: Mycoplasma pneumoniae

<400> SEQUENCE: 40

```
Gly Leu Met Ser Lys Ser Phe Asn Tyr Glu Arg Asn Asn Gln Ser Lys
1               5                   10                  15

Ile Ile Lys Asp Thr Ile Glu Val Pro Ile Lys His Ser Phe Leu Glu
            20                  25                  30

Gly Leu Thr Ile Asn Glu Tyr Phe Asn Ser Ser Tyr Gly Ala Arg Lys
        35                  40                  45

Gly Met Thr Asp Thr Ala Met Lys Thr Ala Lys Ser Gly Tyr Met Thr
    50                  55                  60

Arg Lys Leu Val Asp Ala Thr His
65                  70
```

<210> SEQ ID NO 41
<211> LENGTH: 14
<212> TYPE: PRT
<213> ORGANISM: Bacillus subtilis

<400> SEQUENCE: 41

```
Ser Ala Ala Lys Asp Val Ile Gln Gly Lys Leu Met Lys Ser
1               5                   10
```

<210> SEQ ID NO 42
<211> LENGTH: 7
<212> TYPE: PRT
<213> ORGANISM: Bacillus subtilis

<400> SEQUENCE: 42

```
Ser Asn Phe Thr Gln Leu Ala
1               5
```

<210> SEQ ID NO 43
<211> LENGTH: 61
<212> TYPE: PRT
<213> ORGANISM: Bacillus subtilis

<400> SEQUENCE: 43

Gly Leu Met Ala Asn Pro Ala Gly Arg Ile Ile Glu Leu Pro Ile Lys
1               5                   10                  15

Ser Ser Phe Arg Glu Gly Leu Thr Val Leu Glu Tyr Phe Ile Ser Thr
            20                  25                  30

His Gly Ala Arg Lys Gly Leu Ala Asp Thr Ala Leu Lys Thr Ala Asp
        35                  40                  45

Ser Gly Tyr Leu Thr Arg Arg Leu Val Asp Val Ala Gln
    50                  55                  60

<210> SEQ ID NO 44
<211> LENGTH: 14
<212> TYPE: PRT
<213> ORGANISM: Staphylococcus aureus

<400> SEQUENCE: 44

Thr Asp Ala Lys Asp Gln Ile Gln Gly Glu Leu Met Gln Ser
1               5                   10

<210> SEQ ID NO 45
<211> LENGTH: 7
<212> TYPE: PRT
<213> ORGANISM: Staphylococcus aureus

<400> SEQUENCE: 45

Ser Asn Phe Thr Gln Leu Ala
1               5

<210> SEQ ID NO 46
<211> LENGTH: 61
<212> TYPE: PRT
<213> ORGANISM: Staphylococcus aureus

<400> SEQUENCE: 46

Gly Leu Met Ala Ala Pro Ser Gly Lys Ile Ile Glu Leu Pro Ile Thr
1               5                   10                  15

Ser Ser Phe Arg Glu Gly Leu Thr Val Leu Glu Tyr Phe Ile Ser Thr
            20                  25                  30

His Gly Ala Arg Lys Gly Leu Ala Asp Thr Ala Leu Lys Thr Ala Asp
        35                  40                  45

Ser Gly Tyr Leu Thr Arg Arg Leu Val Asp Val Ala Gln
    50                  55                  60

<210> SEQ ID NO 47
<211> LENGTH: 14
<212> TYPE: PRT
<213> ORGANISM: Mycobacterium tuberculosis

<400> SEQUENCE: 47

Lys Glu Ala Thr Asp Glu Val Gly Gln Ala Leu Arg Glu His
1               5                   10

<210> SEQ ID NO 48
<211> LENGTH: 7
<212> TYPE: PRT
<213> ORGANISM: Mycobacterium tuberculosis

<400> SEQUENCE: 48

Thr Gln Thr Arg Thr Leu Ala
1               5

<210> SEQ ID NO 49
<211> LENGTH: 61
<212> TYPE: PRT
<213> ORGANISM: Mycobacterium tuberculosis

<400> SEQUENCE: 49

Gly Leu Val Thr Asn Pro Lys Gly Glu Phe Ile Pro Arg Pro Val Lys
1               5                   10                  15

Ser Ser Phe Arg Glu Gly Leu Thr Val Leu Glu Tyr Phe Ile Asn Thr
            20                  25                  30

His Gly Ala Arg Lys Gly Leu Ala Asp Thr Ala Leu Arg Thr Ala Asp
        35                  40                  45

Ser Gly Tyr Leu Thr Arg Arg Leu Val Asp Val Ser Gln
    50                  55                  60

<210> SEQ ID NO 50
<211> LENGTH: 14
<212> TYPE: PRT
<213> ORGANISM: Synechocystis sp.

<400> SEQUENCE: 50

Asn Gly Thr Ser Glu Glu Leu Lys Asp Gln Val Val Val Asn
1               5                   10

<210> SEQ ID NO 51
<211> LENGTH: 7
<212> TYPE: PRT
<213> ORGANISM: Synechocystis sp.

<400> SEQUENCE: 51

Ser Gln Val Arg Gln Leu Val
1               5

<210> SEQ ID NO 52
<211> LENGTH: 61
<212> TYPE: PRT
<213> ORGANISM: Synechocystis sp.

<400> SEQUENCE: 52

Gly Leu Met Ala Asp Pro Gln Gly Glu Ile Ile Asp Leu Pro Ile Lys
1               5                   10                  15

Thr Asn Phe Arg Glu Gly Leu Thr Val Thr Glu Tyr Val Ile Ser Ser
            20                  25                  30

Tyr Gly Ala Arg Lys Gly Leu Val Asp Thr Ala Leu Arg Thr Ala Asp
        35                  40                  45

Ser Gly Tyr Leu Thr Arg Arg Leu Val Asp Val Ser Gln
    50                  55                  60

<210> SEQ ID NO 53
<211> LENGTH: 14
<212> TYPE: PRT
<213> ORGANISM: Aquifex aeolicus

<400> SEQUENCE: 53

Ser Glu Ala Thr Asn Leu Val Ser Lys Ala Met Phe Glu Glu
1               5                   10

<210> SEQ ID NO 54
<211> LENGTH: 7
<212> TYPE: PRT
<213> ORGANISM: Aquifex aeolicus

```
<400> SEQUENCE: 54

Asp Gln Ile Arg Gln Leu Ala
1               5

<210> SEQ ID NO 55
<211> LENGTH: 61
<212> TYPE: PRT
<213> ORGANISM: Aquifex aeolicus

<400> SEQUENCE: 55

Gly Leu Met Ala Lys His Ser Gly Glu Phe Ile Glu Thr Pro Ile Ile
1               5                   10                  15

Ser Asn Phe Arg Glu Gly Leu Ser Val Leu Glu Tyr Phe Ile Ser Thr
            20                  25                  30

Tyr Gly Ala Arg Lys Gly Leu Ala Asp Thr Ala Leu Lys Thr Ala Phe
        35                  40                  45

Ala Gly Tyr Leu Thr Arg Arg Leu Val Asp Val Ala Gln
    50                  55                  60

<210> SEQ ID NO 56
<211> LENGTH: 14
<212> TYPE: PRT
<213> ORGANISM: Deinococcus radiodurans

<400> SEQUENCE: 56

Asn Asn Thr Thr Asp Ala Val Lys Asp Ala Val Phe Glu Asn
1               5                   10

<210> SEQ ID NO 57
<211> LENGTH: 7
<212> TYPE: PRT
<213> ORGANISM: Deinococcus radiodurans

<400> SEQUENCE: 57

Gln Gln Ile Arg Gln Leu Ala
1               5

<210> SEQ ID NO 58
<211> LENGTH: 61
<212> TYPE: PRT
<213> ORGANISM: Deinococcus radiodurans

<400> SEQUENCE: 58

Gly Leu Met Ala Arg Pro Asp Gly Ser Thr Ile Glu Val Pro Ile Arg
1               5                   10                  15

Ala Ser Phe Arg Glu Gly Leu Thr Val Leu Glu Tyr Phe Ile Ser Thr
            20                  25                  30

His Gly Ala Arg Lys Gly Ala Asp Thr Ala Leu Arg Thr Ala Asp
        35                  40                  45

Ser Gly Tyr Leu Thr Arg Lys Leu Val Asp Val Ala His
    50                  55                  60

<210> SEQ ID NO 59
<211> LENGTH: 14
<212> TYPE: PRT
<213> ORGANISM: Thermus aquaticus

<400> SEQUENCE: 59

Thr Glu Thr Thr Glu Lys Val Thr Gln Ala Val Phe Lys Asn
1               5                   10
```

<210> SEQ ID NO 60
<211> LENGTH: 7
<212> TYPE: PRT
<213> ORGANISM: Thermus aquaticus

<400> SEQUENCE: 60

Gln Gln Ile Arg Gln Leu Cys
1               5

<210> SEQ ID NO 61
<211> LENGTH: 61
<212> TYPE: PRT
<213> ORGANISM: Thermus aquaticus

<400> SEQUENCE: 61

Gly Leu Met Gln Lys Pro Ser Gly Glu Thr Phe Glu Val Pro Val Arg
1               5                   10                  15

Ser Ser Phe Arg Glu Gly Leu Thr Val Leu Glu Tyr Phe Ile Ser Ser
                20                  25                  30

His Gly Ala Arg Lys Gly Ala Asp Thr Ala Leu Arg Thr Ala Asp
        35                  40                  45

Ser Gly Tyr Leu Thr Arg Lys Leu Val Asp Val Ala His
    50                  55                  60

<210> SEQ ID NO 62
<211> LENGTH: 14
<212> TYPE: PRT
<213> ORGANISM: Thermus thermophilus

<400> SEQUENCE: 62

Thr Glu Thr Thr Glu Lys Val Thr Gln Ala Val Phe Lys Asn
1               5                   10

<210> SEQ ID NO 63
<211> LENGTH: 7
<212> TYPE: PRT
<213> ORGANISM: Thermus thermophilus

<400> SEQUENCE: 63

Gln Gln Ile Arg Gln Leu Cys
1               5

<210> SEQ ID NO 64
<211> LENGTH: 61
<212> TYPE: PRT
<213> ORGANISM: Thermus thermophilus

<400> SEQUENCE: 64

Gly Leu Met Gln Lys Pro Ser Gly Glu Thr Phe Glu Val Pro Val Arg
1               5                   10                  15

Ser Ser Phe Arg Glu Gly Leu Thr Val Leu Glu Tyr Phe Ile Ser Ser
                20                  25                  30

His Gly Ala Arg Lys Gly Ala Asp Thr Ala Leu Arg Thr Ala Asp
        35                  40                  45

Ser Gly Tyr Leu Thr Arg Lys Leu Val Asp Val Thr His
    50                  55                  60

<210> SEQ ID NO 65
<211> LENGTH: 14
<212> TYPE: PRT
<213> ORGANISM: Homo sapiens

<400> SEQUENCE: 65

```
Asn Met Ile Asp Leu Lys Phe Lys Glu Glu Val Asn His Tyr
1               5                   10
```

<210> SEQ ID NO 66
<211> LENGTH: 7
<212> TYPE: PRT
<213> ORGANISM: Homo sapiens

<400> SEQUENCE: 66

```
Val Asn Thr Met Gln Ile Ser
1               5
```

<210> SEQ ID NO 67
<211> LENGTH: 81
<212> TYPE: PRT
<213> ORGANISM: Homo sapiens

<400> SEQUENCE: 67

```
Gly Gln Ile Glu Leu Glu Gly Arg Ser Thr Pro Leu Met Ala Ser Gly
1               5                   10                  15

Lys Ser Leu Pro Cys Phe Glu Pro Tyr Glu Phe Thr Pro Arg Ala Gly
            20                  25                  30

Gly Phe Val Thr Gly Arg Phe Leu Thr Gly Ile Lys Pro Pro Glu Phe
        35                  40                  45

Phe Phe His Cys Met Ala Gly Arg Glu Gly Leu Val Asp Thr Ala Val
    50                  55                  60

Lys Thr Ser Arg Ser Gly Tyr Leu Gln Arg Cys Ile Ile Lys His Leu
65                  70                  75                  80

Glu
```

<210> SEQ ID NO 68
<211> LENGTH: 14
<212> TYPE: PRT
<213> ORGANISM: Homo sapiens

<400> SEQUENCE: 68

```
Glu Asn Gln Val Asn Arg Ile Leu Asn Asp Ala Arg Asp Lys
1               5                   10
```

<210> SEQ ID NO 69
<211> LENGTH: 7
<212> TYPE: PRT
<213> ORGANISM: Homo sapiens

<400> SEQUENCE: 69

```
Ile Asn Ile Ser Gln Val Ile
1               5
```

<210> SEQ ID NO 70
<211> LENGTH: 81
<212> TYPE: PRT
<213> ORGANISM: Homo sapiens

<400> SEQUENCE: 70

```
Gly Gln Gln Asn Val Glu Gly Lys Arg Ile Pro Phe Gly Phe Lys His
1               5                   10                  15

Arg Thr Leu Pro His Phe Ile Lys Asp Asp Tyr Gly Pro Glu Ser Arg
            20                  25                  30

Gly Phe Val Glu Asn Ser Tyr Leu Ala Gly Leu Thr Pro Thr Glu Phe
        35                  40                  45
```

```
Phe Phe His Ala Met Gly Gly Arg Glu Gly Leu Ile Asp Thr Ala Val
        50                  55                  60

Lys Thr Ala Glu Thr Gly Tyr Ile Gln Arg Arg Leu Ile Lys Ser Met
 65                  70                  75                  80

Glu

<210> SEQ ID NO 71
<211> LENGTH: 14
<212> TYPE: PRT
<213> ORGANISM: Homo sapiens

<400> SEQUENCE: 71

Glu Ala Leu Ile Leu Lys Glu Leu Ser Val Ile Arg Asp His
  1               5                  10

<210> SEQ ID NO 72
<211> LENGTH: 7
<212> TYPE: PRT
<213> ORGANISM: Homo sapiens

<400> SEQUENCE: 72

Ile Asn Ile Ser Gln Met Ile
  1               5

<210> SEQ ID NO 73
<211> LENGTH: 81
<212> TYPE: PRT
<213> ORGANISM: Homo sapiens

<400> SEQUENCE: 73

Gly Gln Gln Ala Ile Ser Gly Ser Arg Val Pro Asp Gly Phe Glu Asn
  1               5                  10                  15

Arg Ser Leu Pro His Phe Glu Lys His Ser Lys Leu Pro Ala Ala Lys
                 20                  25                  30

Gly Phe Val Ala Asn Ser Phe Tyr Ser Gly Leu Thr Pro Thr Glu Phe
             35                  40                  45

Phe Phe His Thr Met Ala Gly Arg Glu Gly Leu Val Asp Thr Ala Val
        50                  55                  60

Lys Thr Ala Glu Thr Gly Tyr Met Gln Arg Arg Leu Val Lys Ser Leu
 65                  70                  75                  80

Glu

<210> SEQ ID NO 74
<211> LENGTH: 7
<212> TYPE: PRT
<213> ORGANISM: Escherichia coli

<400> SEQUENCE: 74

Gly Pro Asn Ile Gly Leu Ile
  1               5

<210> SEQ ID NO 75
<211> LENGTH: 9
<212> TYPE: PRT
<213> ORGANISM: Escherichia coli

<400> SEQUENCE: 75

Glu His Asp Asp Ala Asn Arg Ala Leu
  1               5

<210> SEQ ID NO 76
```

```
<211> LENGTH: 7
<212> TYPE: PRT
<213> ORGANISM: Haemophilus influenzae

<400> SEQUENCE: 76

Gly Pro Asn Ile Gly Leu Ile
1               5

<210> SEQ ID NO 77
<211> LENGTH: 9
<212> TYPE: PRT
<213> ORGANISM: Haemophilus influenzae

<400> SEQUENCE: 77

Glu His Asp Asp Ala Asn Arg Ala Leu
1               5

<210> SEQ ID NO 78
<211> LENGTH: 7
<212> TYPE: PRT
<213> ORGANISM: Vibrio cholerae

<400> SEQUENCE: 78

Gly Pro Asn Ile Gly Leu Ile
1               5

<210> SEQ ID NO 79
<211> LENGTH: 9
<212> TYPE: PRT
<213> ORGANISM: Vibrio cholerae

<400> SEQUENCE: 79

Glu His Asp Asp Ala Asn Arg Ala Leu
1               5

<210> SEQ ID NO 80
<211> LENGTH: 7
<212> TYPE: PRT
<213> ORGANISM: Pseudomonas aeruginosa

<400> SEQUENCE: 80

Gly Pro Asn Ile Gly Leu Ile
1               5

<210> SEQ ID NO 81
<211> LENGTH: 9
<212> TYPE: PRT
<213> ORGANISM: Pseudomonas aeruginosa

<400> SEQUENCE: 81

Glu His Asp Asp Ala Asn Arg Ala Leu
1               5

<210> SEQ ID NO 82
<211> LENGTH: 7
<212> TYPE: PRT
<213> ORGANISM: Treponema pallidum

<400> SEQUENCE: 82

Gly Pro Asn Ile Gly Leu Ile
1               5

<210> SEQ ID NO 83
<211> LENGTH: 9
<212> TYPE: PRT
```

```
<213> ORGANISM: Treponema pallidum

<400> SEQUENCE: 83

Glu His Asp Asp Ala Asn Arg Ala Leu
1               5

<210> SEQ ID NO 84
<211> LENGTH: 7
<212> TYPE: PRT
<213> ORGANISM: Borrelia burgdorferi

<400> SEQUENCE: 84

Gly Pro Asn Ile Gly Leu Ile
1               5

<210> SEQ ID NO 85
<211> LENGTH: 9
<212> TYPE: PRT
<213> ORGANISM: Borrelia burgdorferi

<400> SEQUENCE: 85

Glu His Asn Asp Ala Asn Arg Ala Leu
1               5

<210> SEQ ID NO 86
<211> LENGTH: 7
<212> TYPE: PRT
<213> ORGANISM: Xylella fastidiosa

<400> SEQUENCE: 86

Gly Pro Asn Ile Gly Leu Ile
1               5

<210> SEQ ID NO 87
<211> LENGTH: 9
<212> TYPE: PRT
<213> ORGANISM: Xylella fastidiosa

<400> SEQUENCE: 87

Glu His Asp Asp Ala Asn Arg Ala Leu
1               5

<210> SEQ ID NO 88
<211> LENGTH: 7
<212> TYPE: PRT
<213> ORGANISM: Campylobacter jejuni

<400> SEQUENCE: 88

Gly Gln Asn Ile Gly Leu Ile
1               5

<210> SEQ ID NO 89
<211> LENGTH: 9
<212> TYPE: PRT
<213> ORGANISM: Campylobacter jejuni

<400> SEQUENCE: 89

Glu His Asp Asp Ala Asn Arg Ala Leu
1               5

<210> SEQ ID NO 90
<211> LENGTH: 7
<212> TYPE: PRT
<213> ORGANISM: Neisseria meningitidis
```

```
<400> SEQUENCE: 90

Gly Pro Asn Ile Gly Leu Ile
1               5

<210> SEQ ID NO 91
<211> LENGTH: 9
<212> TYPE: PRT
<213> ORGANISM: Neisseria meningitidis

<400> SEQUENCE: 91

Glu His Asp Asp Ala Asn Arg Ala Leu
1               5

<210> SEQ ID NO 92
<211> LENGTH: 7
<212> TYPE: PRT
<213> ORGANISM: Rickettsia prowazekii

<400> SEQUENCE: 92

Gly Gln Asn Ile Gly Leu Ile
1               5

<210> SEQ ID NO 93
<211> LENGTH: 9
<212> TYPE: PRT
<213> ORGANISM: Rickettsia prowazekii

<400> SEQUENCE: 93

Glu Asn Asp Asp Ala Asn Arg Ala Leu
1               5

<210> SEQ ID NO 94
<211> LENGTH: 7
<212> TYPE: PRT
<213> ORGANISM: Chlamydia trachomatis

<400> SEQUENCE: 94

Gly Pro Asn Ile Gly Leu Ile
1               5

<210> SEQ ID NO 95
<211> LENGTH: 9
<212> TYPE: PRT
<213> ORGANISM: Chlamydia trachomatis

<400> SEQUENCE: 95

Glu His Asp Asp Ala Asn Arg Ala Leu
1               5

<210> SEQ ID NO 96
<211> LENGTH: 7
<212> TYPE: PRT
<213> ORGANISM: Mycoplasma pneumoniae

<400> SEQUENCE: 96

Gly Met Asn Ile Gly Leu Ile
1               5

<210> SEQ ID NO 97
<211> LENGTH: 9
<212> TYPE: PRT
<213> ORGANISM: Mycoplasma pneumoniae

<400> SEQUENCE: 97
```

Glu Asn Asp Asp Ser Ala Arg Ala Leu
1               5

<210> SEQ ID NO 98
<211> LENGTH: 7
<212> TYPE: PRT
<213> ORGANISM: Bacillus subtilis

<400> SEQUENCE: 98

Gly Pro Asn Ile Gly Leu Ile
1               5

<210> SEQ ID NO 99
<211> LENGTH: 9
<212> TYPE: PRT
<213> ORGANISM: Bacillus subtilis

<400> SEQUENCE: 99

Glu Asn Asp Asp Ser Asn Arg Ala Leu
1               5

<210> SEQ ID NO 100
<211> LENGTH: 7
<212> TYPE: PRT
<213> ORGANISM: Staphylococcus aureus

<400> SEQUENCE: 100

Gly Pro Asn Ile Gly Leu Ile
1               5

<210> SEQ ID NO 101
<211> LENGTH: 9
<212> TYPE: PRT
<213> ORGANISM: Staphylococcus aureus

<400> SEQUENCE: 101

Glu Asn Asp Asp Ser Asn Arg Ala Leu
1               5

<210> SEQ ID NO 102
<211> LENGTH: 7
<212> TYPE: PRT
<213> ORGANISM: Mycobacterium tuberculosis

<400> SEQUENCE: 102

Gly Pro Asn Ile Gly Leu Ile
1               5

<210> SEQ ID NO 103
<211> LENGTH: 9
<212> TYPE: PRT
<213> ORGANISM: Mycobacterium tuberculosis

<400> SEQUENCE: 103

Glu His Asp Asp Ala Asn Arg Ala Leu
1               5

<210> SEQ ID NO 104
<211> LENGTH: 7
<212> TYPE: PRT
<213> ORGANISM: Synechocystis sp.

<400> SEQUENCE: 104

Gly Pro Asn Ala Gly Leu Ile
1               5

<210> SEQ ID NO 105
<211> LENGTH: 9
<212> TYPE: PRT
<213> ORGANISM: Synechocystis sp.

<400> SEQUENCE: 105

Glu His Asp Asp Ala Asn Arg Ala Leu
1               5

<210> SEQ ID NO 106
<211> LENGTH: 7
<212> TYPE: PRT
<213> ORGANISM: Aquifex aeolicus

<400> SEQUENCE: 106

Gly Gln Asn Ile Gly Leu Val
1               5

<210> SEQ ID NO 107
<211> LENGTH: 9
<212> TYPE: PRT
<213> ORGANISM: Aquifex aeolicus

<400> SEQUENCE: 107

Glu His Asp Asp Ala Asn Arg Ala Leu
1               5

<210> SEQ ID NO 108
<211> LENGTH: 7
<212> TYPE: PRT
<213> ORGANISM: Deinococcus radiodurans

<400> SEQUENCE: 108

Gly Ala Asn Ile Gly Leu Ile
1               5

<210> SEQ ID NO 109
<211> LENGTH: 9
<212> TYPE: PRT
<213> ORGANISM: Deinococcus radiodurans

<400> SEQUENCE: 109

Glu His Asp Asp Ala Asn Arg Ala Leu
1               5

<210> SEQ ID NO 110
<211> LENGTH: 7
<212> TYPE: PRT
<213> ORGANISM: Thermus thermophilus

<400> SEQUENCE: 110

Gly Ala Asn Ile Gly Leu Ile
1               5

<210> SEQ ID NO 111
<211> LENGTH: 9
<212> TYPE: PRT
<213> ORGANISM: Thermus thermophilus

<400> SEQUENCE: 111

Glu His Asp Asp Ala Asn Arg Ala Leu
1               5

-continued

```
<210> SEQ ID NO 112
<211> LENGTH: 7
<212> TYPE: PRT
<213> ORGANISM: Thermus aquaticus

<400> SEQUENCE: 112

Gly Ala Asn Ile Gly Leu Ile
1               5

<210> SEQ ID NO 113
<211> LENGTH: 9
<212> TYPE: PRT
<213> ORGANISM: Thermus aquaticus

<400> SEQUENCE: 113

Glu His Asp Asp Ala Asn Arg Ala Leu
1               5

<210> SEQ ID NO 114
<211> LENGTH: 7
<212> TYPE: PRT
<213> ORGANISM: Homo sapiens

<400> SEQUENCE: 114

Gly Glu Pro Cys Gly Leu Met
1               5

<210> SEQ ID NO 115
<211> LENGTH: 9
<212> TYPE: PRT
<213> ORGANISM: Homo sapiens

<400> SEQUENCE: 115

Asp His Asn Gln Ser Pro Arg Asn Met
1               5

<210> SEQ ID NO 116
<211> LENGTH: 7
<212> TYPE: PRT
<213> ORGANISM: Homo sapiens

<400> SEQUENCE: 116

Gly His Ala Val Gly Leu Val
1               5

<210> SEQ ID NO 117
<211> LENGTH: 9
<212> TYPE: PRT
<213> ORGANISM: Homo sapiens

<400> SEQUENCE: 117

Asp His Asn Gln Ser Pro Arg Asn Thr
1               5

<210> SEQ ID NO 118
<211> LENGTH: 7
<212> TYPE: PRT
<213> ORGANISM: Homo sapiens

<400> SEQUENCE: 118

Gly Glu Ala Cys Gly Leu Val
1               5

<210> SEQ ID NO 119
<211> LENGTH: 9
```

```
<212> TYPE: PRT
<213> ORGANISM: Homo sapiens

<400> SEQUENCE: 119

His His Asn Gln Ser Pro Arg Asn Thr
1               5
```